US009936966B2

(12) United States Patent
Castro

(10) Patent No.: US 9,936,966 B2
(45) Date of Patent: Apr. 10, 2018

(54) END EFFECTOR CONNECTION AND ACTUATION SYSTEMS

(71) Applicant: Teleflex Medical Incorporated, Research Triangle Park, NC (US)

(72) Inventor: Salvatore Castro, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 303 days.

(21) Appl. No.: 14/175,413

(22) Filed: Feb. 7, 2014

(65) Prior Publication Data
US 2014/0216187 A1 Aug. 7, 2014

Related U.S. Application Data

(60) Provisional application No. 61/762,154, filed on Feb. 7, 2013.

(51) Int. Cl.
*A61B 17/00* (2006.01)
*A61B 17/29* (2006.01)

(52) U.S. Cl.
CPC ...... *A61B 17/29* (2013.01); *A61B 2017/0046* (2013.01); *A61B 2017/00477* (2013.01); *A61B 2017/292* (2013.01); *A61B 2017/2931* (2013.01); *A61B 2017/2939* (2013.01); *Y10T 29/49826* (2015.01); *Y10T 74/1892* (2015.01)

(58) Field of Classification Search
CPC .... A61B 2017/00477; A61B 2017/292; A61B 2017/2931; A61B 2017/2946; A61B 17/29
See application file for complete search history.

(56) References Cited

U.S. PATENT DOCUMENTS

| 5,366,477 | A | * | 11/1994 | LeMarie, III | A61B 17/29 403/336 |
| 5,676,678 | A | * | 10/1997 | Schad | A61B 17/29 606/170 |
| 8,764,735 | B2 | | 7/2014 | Coe et al. | |
| 2008/0243106 | A1 | * | 10/2008 | Coe | A61B 17/00234 606/1 |

(Continued)

FOREIGN PATENT DOCUMENTS

| JP | 07255734 A | 10/1995 |
| JP | 2003175047 A | 6/2003 |
| JP | 2006-280932 A | 10/2006 |

OTHER PUBLICATIONS

International Search Report dated May 22, 2014.

*Primary Examiner* — Gregory Anderson
*Assistant Examiner* — Christina Lauer
(74) *Attorney, Agent, or Firm* — Baker Hostetler LLP

(57) ABSTRACT

An end effector actuation system includes a shaft assembly having an outer shaft with an internal lumen and an actuation rod slidably received in the lumen, the outer shaft having a distal end portion that is compressible only when the actuation rod is absent from the lumen in the distal end portion, a locking boss provided on the distal end portion; and an end effector assembly having a receiving opening and a retention pocket, wherein the receiving opening is sized to receive the compressed distal end portion of the outer shaft and the retention pocket is sized to receive the locking boss when the distal end portion is uncompressed due to the presence of the actuation rod in the lumen of the distal end portion.

19 Claims, 21 Drawing Sheets

(56) References Cited

U.S. PATENT DOCUMENTS

| | | |
|---|---|---|
| 2009/0131932 A1 | 5/2009 | Vakharia et al. |
| 2010/0094083 A1 | 4/2010 | Taylor et al. |
| 2010/0168723 A1 | 7/2010 | Suarez et al. |
| 2011/0087265 A1 | 4/2011 | Nobis et al. |
| 2012/0059408 A1 | 3/2012 | Mueller |
| 2013/0172859 A1* | 7/2013 | Kaercher ......... A61B 17/00234 606/1 |
| 2014/0001232 A1 | 1/2014 | Cappola et al. |
| 2014/0001233 A1 | 1/2014 | Cappola et al. |
| 2014/0088637 A1* | 3/2014 | Parihar ................. A61B 17/29 606/205 |

* cited by examiner

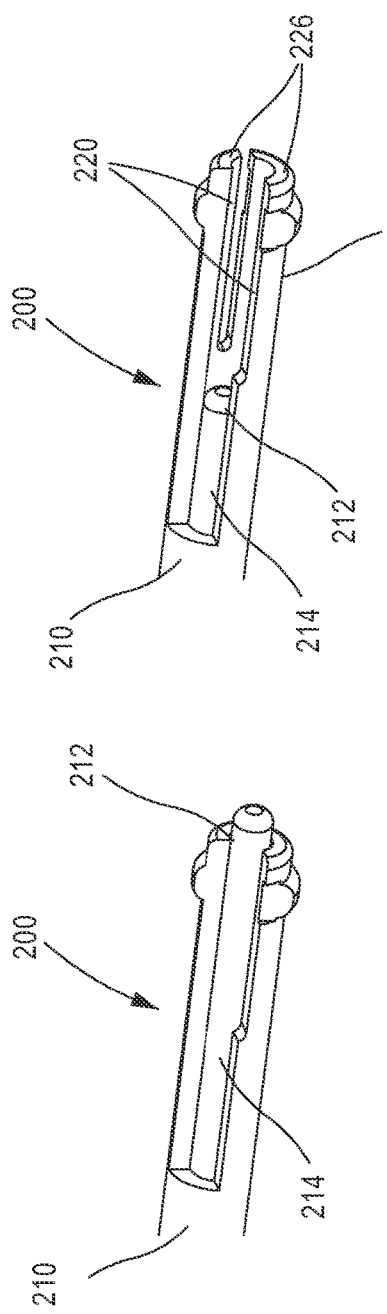
FIG. 12
FIG. 13
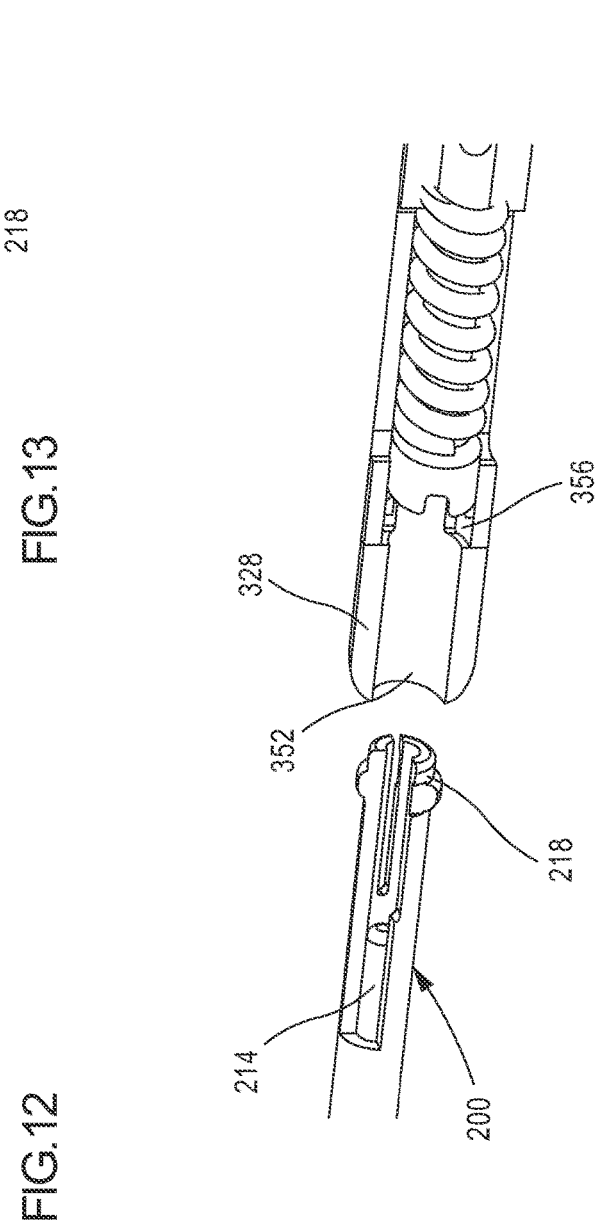
FIG. 14

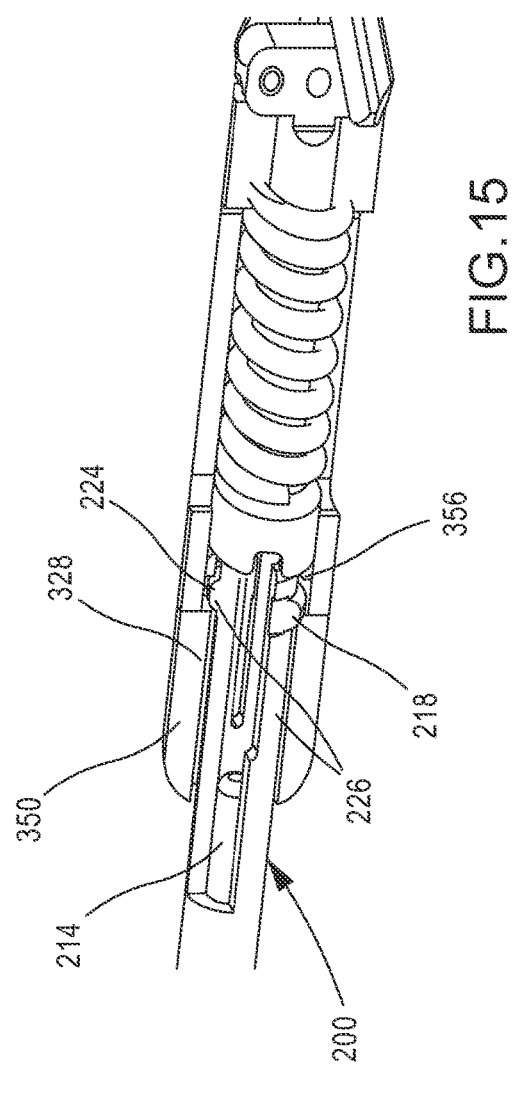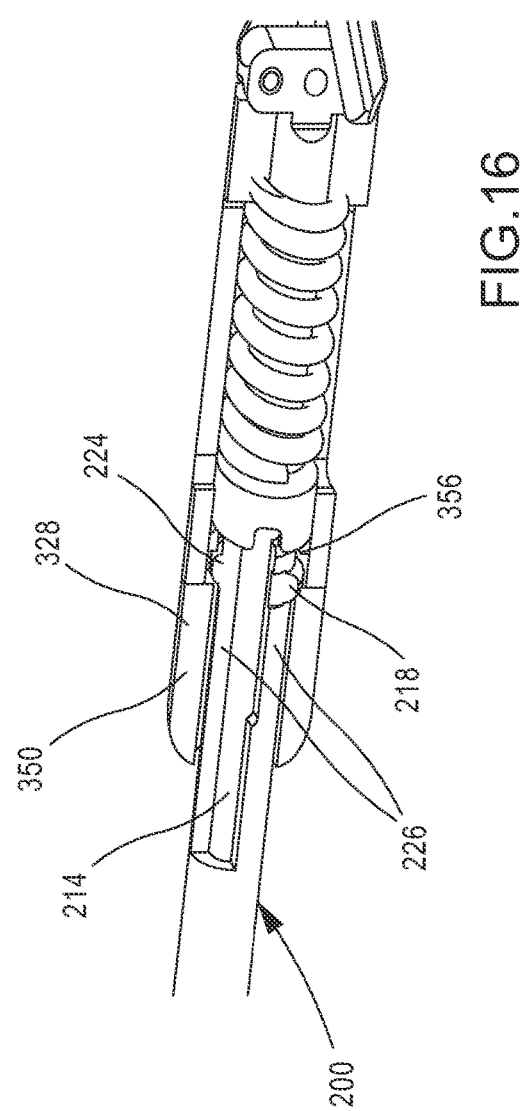

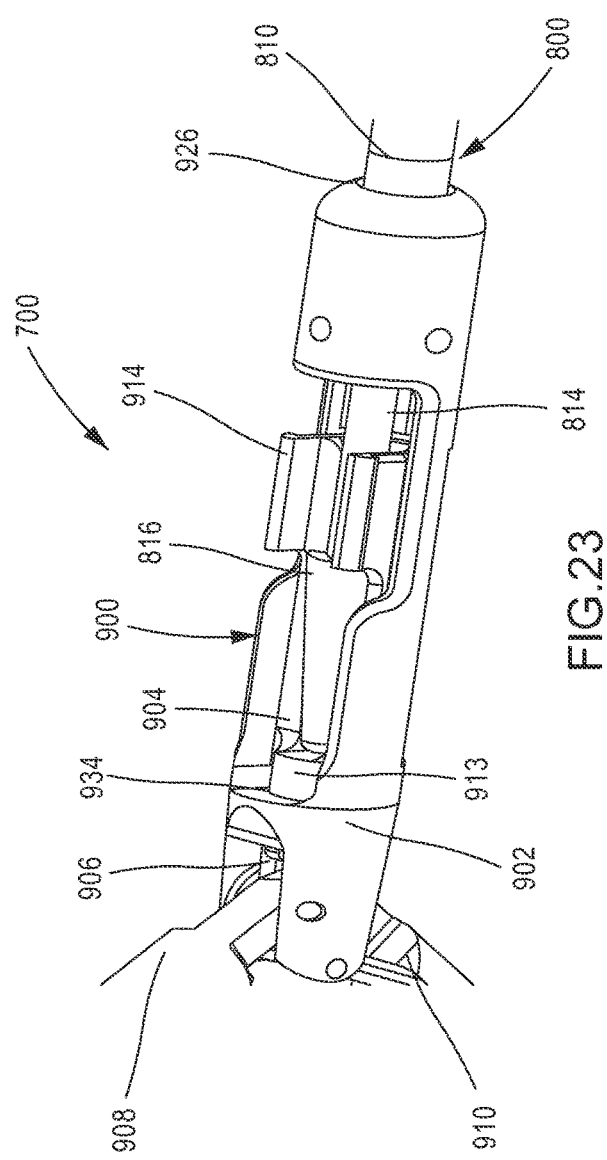
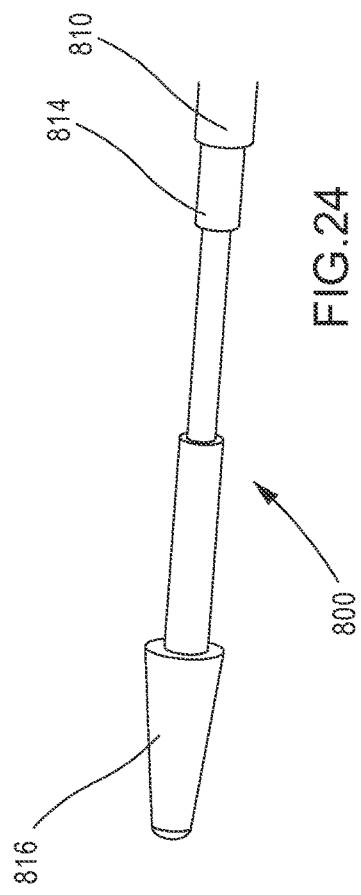

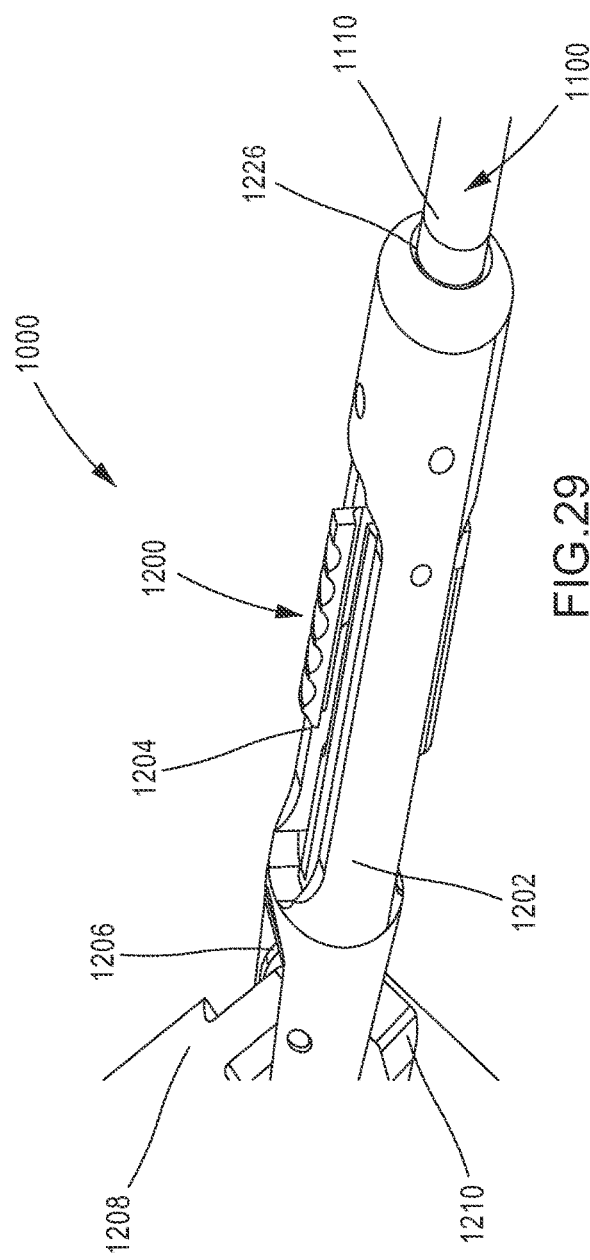
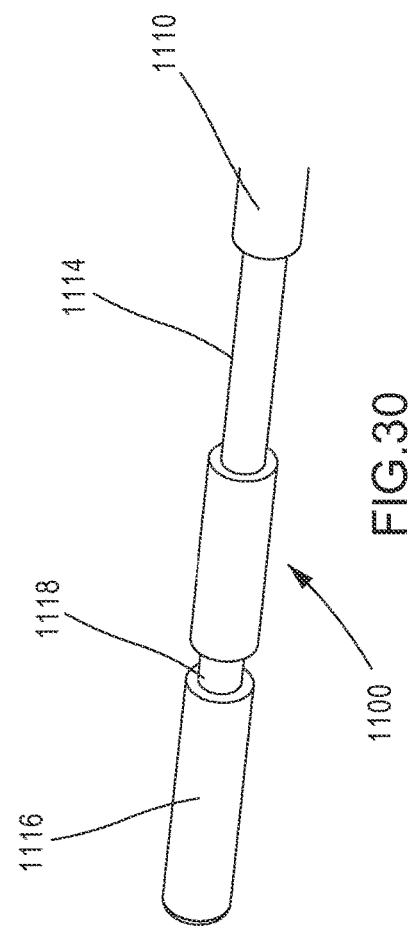

END EFFECTOR CONNECTION AND ACTUATION SYSTEMS

CROSS-REFERENCE TO RELATED APPLICATIONS

This application claims priority to U.S. Provisional Patent Application No. 61/762,154, entitled, "END EFFECTOR CONNECTION AND ACTUATION SYSTEMS," filed Feb. 7, 2013, which is hereby incorporated by reference in its entirety.

FIELD OF THE DISCLOSURE

The disclosure generally relates to end effector systems for minimally invasive surgical techniques. More particularly, the subject matter disclosed herein relates to end effector connection and actuation systems.

BACKGROUND OF THE DISCLOSURE

Minimally invasive surgical procedures, such as laparoscopic or endoscopic procedures, are becoming more and more common. Surgeons today are often able to perform complex procedures using tools inserted through relatively small entry points in the body, often reducing patient scarring and recovery time. These surgical tools often have a very specific function and include, for example, scissors, graspers, dissectors, sealers, suture aids, retractors, clamps and clip appliers. Often an endoscope, which is an instrument that allows visual inspection and magnification of interior portions of the body, is used in conjunction with these various tools to perform a procedure.

The tools and instruments for minimally invasive surgery are often inserted into the body through a cannula or trocar. A hole is made through the body's soft tissue to gain access to a body cavity, for example. The hole may made with an obturator instrument or a trocar having a cutting instrument integrally formed or provided therewith.

End effector assemblies refer to the often interchangeable portions of a surgical instrument that contact and manipulate tissues in a patient. Conventional surgical instruments have a hollow shaft with a solid actuating rod slidably provided therein to actuate one of these end effector assemblies that is typically coupled to the hollow shaft. The rod is usually coupled at a proximal end to an instrument actuation device, such as a handle, that when operated slides the rod through the hollow shaft to actuate the end effector assembly.

A need exists for methods and systems that will provide the capability to easily, quickly and effectively couple or decouple an end effector assembly to the instrument shaft.

SUMMARY OF THE DISCLOSURE

The foregoing needs are met, to a great extent, by the present disclosure, wherein in one aspect, an end effector actuation system includes a shaft assembly having an outer shaft with an internal lumen and an actuation rod slidably received in the lumen, the outer shaft having a distal end portion that is compressible only when the actuation rod is absent from the lumen in the distal end portion. A locking boss is provided on the distal end portion of the outer shaft and an end effector assembly is provided that has a receiving opening and a retention pocket, wherein the receiving opening is sized to receive the compressed distal end portion of the outer shaft and the retention pocket is sized to receive the locking boss when the distal end portion is uncompressed due to the presence of the actuation rod in the lumen of the distal end portion.

In accordance with other aspects of the present disclosure, an end effector actuation system includes a shaft assembly having an outer shaft and an actuation shaft slidably received in the outer shaft, the actuation shaft having a tip end, and an end effector assembly including a clevis housing, a tip connector for securing the tip end of the actuation shaft, and a jaws assembly coupled to the tip connector, wherein the tip connector is housed in the clevis housing and has an expandable portion, the expandable portion being expandable only when the tip connector is at a predetermined position in the clevis housing.

In accordance with yet other aspects of the present disclosure, a method of connecting an end effector to an actuation shaft includes providing a shaft assembly comprising an outer shaft having a compressible distal end portion configured with at least one locking boss; an actuation shaft slidably accommodated in the outer shaft, one end of the actuation shaft configured to slidably extend and retract from the distal end portion of the outer shaft; providing an end effector assembly having a receiving opening and a retention pocket for mating with the locking boss; with the actuation shaft substantially retracted from the distal end portion of the shaft assembly, inserting the distal end portion of the shaft assembly into the receiving opening of the end effector to force compression of the distal end portion until the locking boss is received in the retention pocket and the distal end portion uncompresses; and actuating the actuation shaft to extend into the distal end portion to prevent compression of the distal end portion.

There has thus been outlined, rather broadly, certain aspects of the invention in order that the detailed description herein may be better understood, and in order that the present contribution to the art may be better appreciated.

In this respect, before explaining at least one embodiment of the invention in detail, it is to be understood that the invention is not limited in its application to the details of the construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 12 is a perspective view of a distal portion of a shaft assembly with a portion of the outer shaft cutaway to illustrate the assembly in a particular state of use, in accordance with aspects of the present disclosure;

FIG. 13 is a perspective view of a distal portion of a shaft assembly with a portion of the outer shaft cutaway to illustrate the assembly in a particular state of use, in accordance with aspects of the present disclosure;

FIG. 14 is a perspective view of a distal portion of a shaft assembly and an end effector assembly with portions cutaway to illustrate a coupling method, in accordance with aspects of the present disclosure;

FIG. 15 is a perspective view of a distal portion of a shaft assembly and an end effector assembly with portions cutaway to illustrate a coupling method, in accordance with aspects of the present disclosure;

FIG. 16 is a perspective view of a distal portion of a shaft assembly and an end effector assembly with portions cutaway to illustrate a coupling method, in accordance with aspects of the present disclosure;

FIG. 23 is a perspective view of another end effector actuation system comprising a shaft assembly and end effector assembly, in accordance with aspects of the present disclosure;

FIG. 24 is a perspective view of another shaft assembly, in accordance with aspects of the present disclosure;

FIG. 29 is a perspective view of another end effector actuation system comprising a shaft assembly and end effector assembly, in accordance with aspects of the present disclosure;

FIG. 30 is a perspective view of another shaft assembly, in accordance with aspects of the present disclosure;

DETAILED DESCRIPTION OF THE DISCLOSURE

Figure 1:
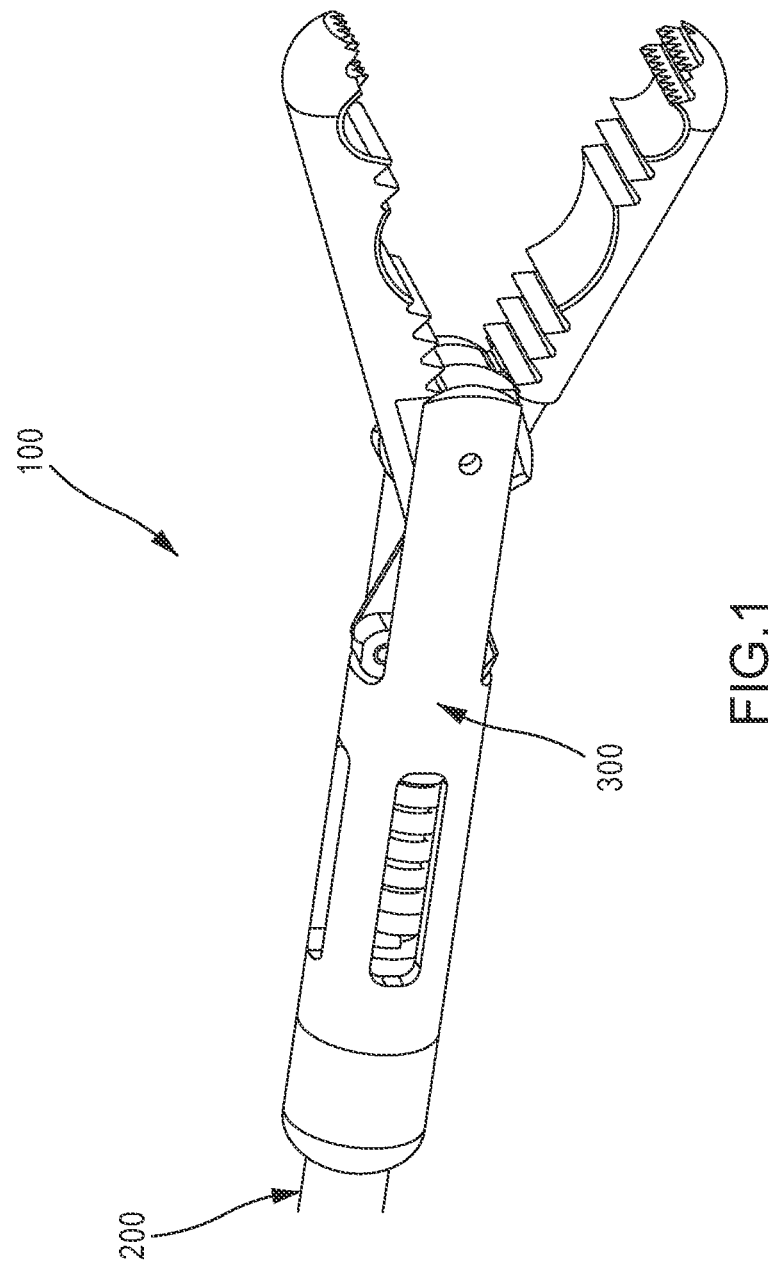
FIG. 1 is a perspective view of an end effector actuation system comprising a shaft assembly and end effector assembly, in accordance with aspects of the present disclosure.

FIG. 1 is a perspective view illustrating an end effector actuation system 100 according to an embodiment of the present disclosure. The actuation system 100 may include a shaft assembly 200 and an end effector assembly 300 coupled together as described below, for example, in order to articulate the end effector assembly 300 manually or robotically in a manner that provides a specific function or capability during a minimally invasive medical procedure.

Figure 2:
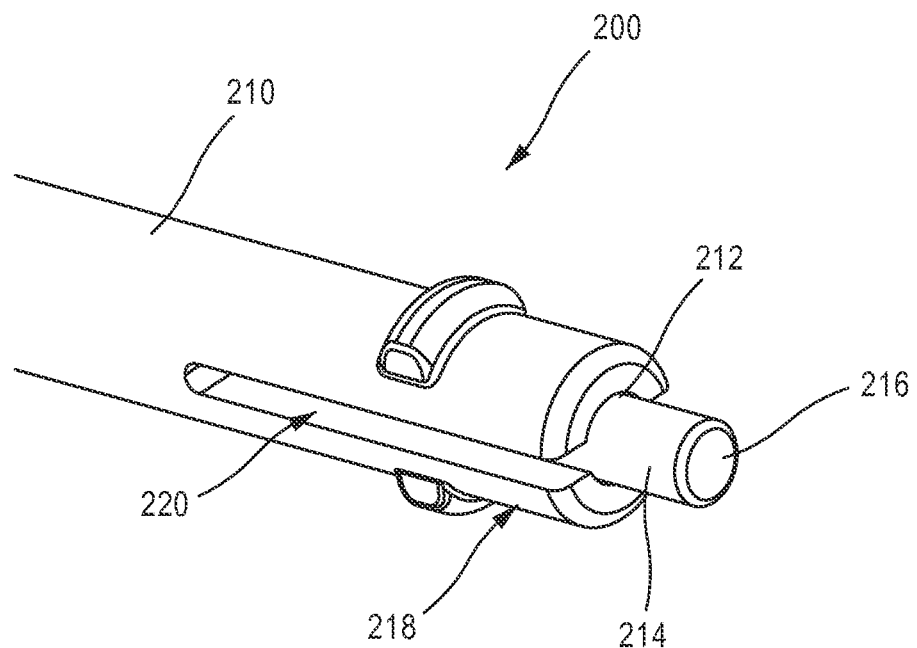
FIG. 2 is an enlarged view of a distal portion of a shaft assembly, in accordance with aspects of the present disclosure.

As shown in FIG. 2, the shaft assembly 200 may include an outer shaft 210 made of a high-quality, durable material, such as stainless steel or a temperature resistant plastic. The outer shaft 210 may be configured to have an outside diameter of approximately 3 mm for coupling with 5 mm end-effector assemblies, for example. The outer shaft 210 may be generally straight and configured with an inner lumen 212 for slidably accommodating an actuation shaft 214. In accordance with other aspects of the present invention, the outer shaft 210 may be curved or flexible as long as the actuation shaft 214 may be properly accommodated in the inner lumen 212 so that a distal end 216 of the actuation shaft 214 may selectively extend out of and retract back into a distal end 218 of the outer shaft 210.

Figure 3:
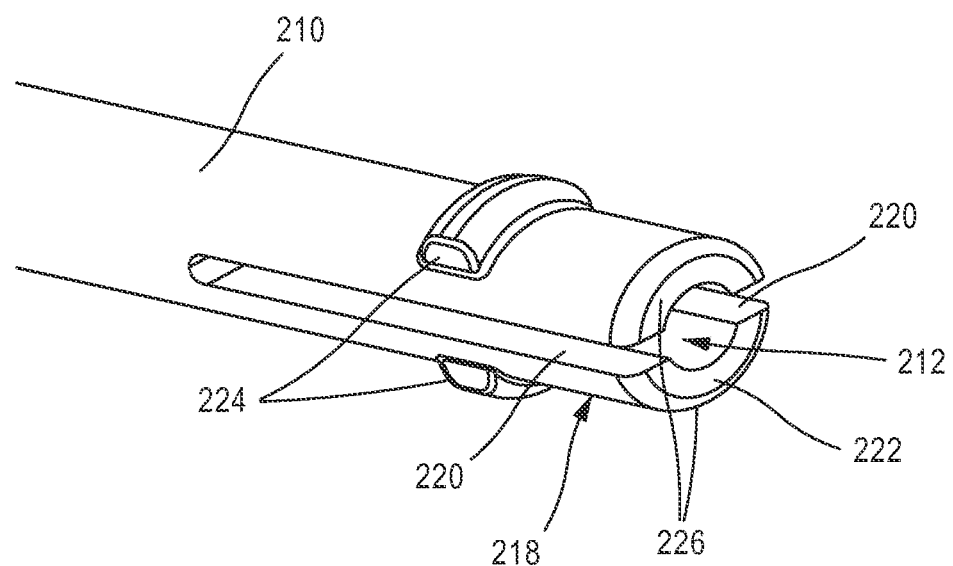
FIG. 3 is an enlarged view of a distal portion of a shaft assembly in a particular state of use, in accordance with aspects of the present disclosure.

As shown more particularly in FIG. 3, the distal end 218 of the outer shaft 210 may be formed with one or more longitudinal flexing slits 220. The flexing slits 220 may extend longitudinally from an end 222 of the outer shaft 210 a predetermined distance. The flexing slits 220 allow the distal end 218 of the shaft 210 to be compressed when the actuation shaft 214 is retracted and/or absent from the distal portion of lumen 212. For example, as shown in FIG. 3, two flexing slits 220 may be formed on diametrically opposed portions of the outer shaft 210 to form two flexing arms 226. The absence of the actuation shaft 214 in the lumen between the flexing arms 226, for example, allows the flexing arms 226 to be compressed toward one another, permitting the distal end 218 of the shaft 210 to assume a smaller diameter than the standard diameter of the shaft 210 that exists when the flexing arms 226 are uncompressed.

One or more locking bosses 224 may be formed to protrude from the outer shaft 210. For example, as shown in FIG. 3, a locking boss 224 may be configured on each of the flexing arms 226 forming the compressible portion of the distal end 218 of the outer shaft 210, i.e., that portion between the end 222 of the outer shaft 210 and the innermost extent of the longitudinal flexing slits 220. The locking bosses 224 may be formed to extend radially to a predetermined height and extend circumferentially around a predetermined portion of the outer shaft 210. The outer edges of the locking bosses 224 may be beveled to allow for the locking bosses to more easily slide past surfaces during coupling/decoupling of the shaft assembly 200 with the end effector assembly 300.

Figure 4:
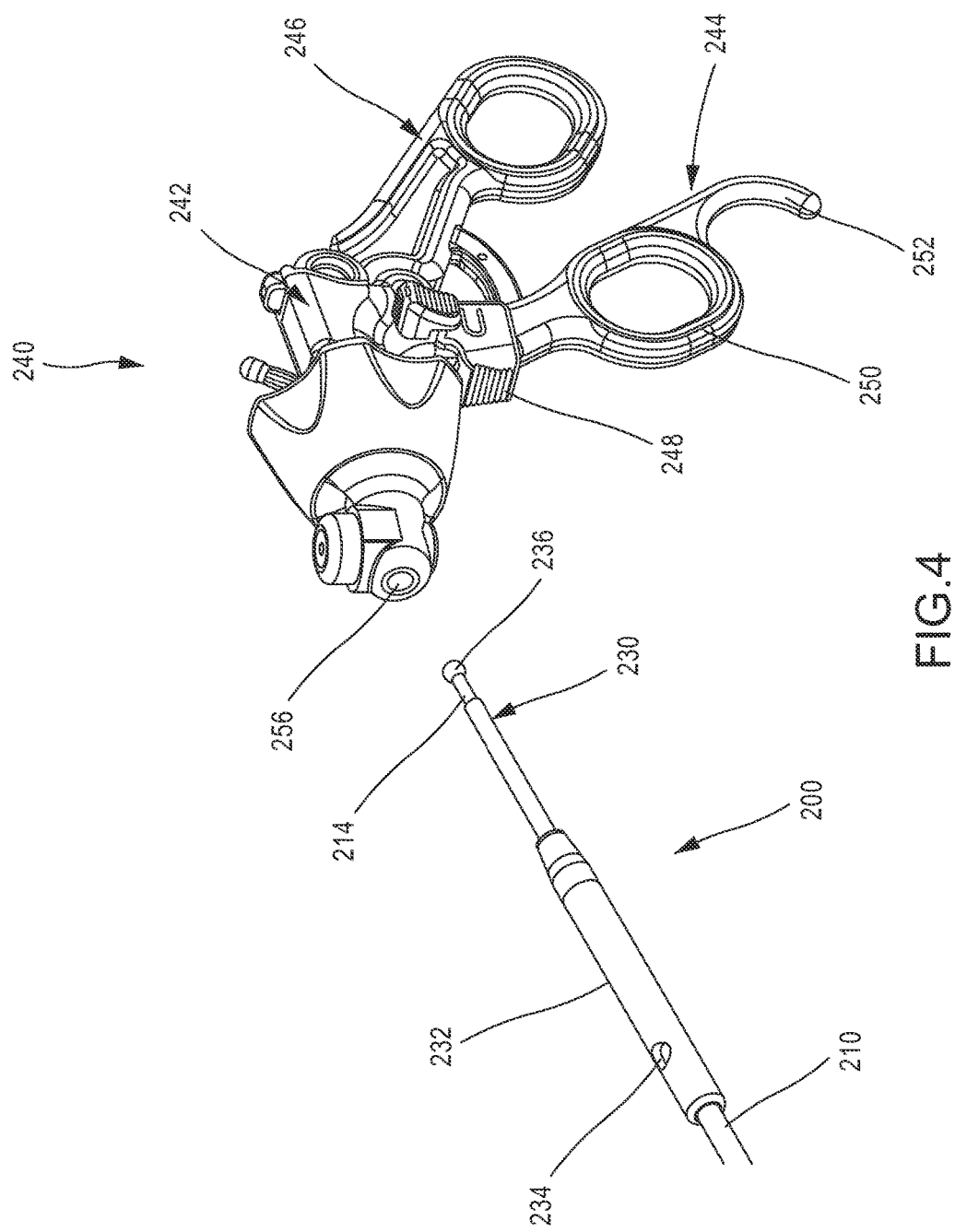
FIG. 4 illustrates a method of coupling a proximal portion of a shaft assembly to an instrument handle, in accordance with aspects of the present disclosure.

As shown in FIG. 4, the proximal end 230 of the outer shaft 210 may be configured to couple to an instrument handle 240, for example, permitting manual manipulation of the actuation shaft 214 to extend or retract from the distal end 218 of the outer shaft. To accommodate a secure coupling with the instrument handle 240, the outer shaft 210 may include a locking sleeve 232 having a shaft lock receptacle 234 and the proximal end of the actuation shaft 214 may be configured with a lock ball 236.

The instrument handle 240 may resemble a pistol grip, for example, having a main body portion 242, a forward finger support 244 and a thumb lever 246. The forward finger support 242 may be rigidly coupled to or integrally formed to extend downward from the main body portion 242. The forward finger support 244 may be ergonomically configured, for example, with multiple finger placement areas 248, 250, and 252 to enable comfortable, effective control of the actuation system during a medical procedure. Placement of the index finger in area 248, the middle finger in area 250, and the ring finger in area 252 provides stable support during manipulation and control of the actuation system. The thumb lever 246 may be rotatably attached to the main body portion 242 and coupled to the lock ball 236 (see FIG. 6) of the actuation shaft 214 in a manner that allows efficient user control over the retraction and extension of the actuation shaft 214 through the outer shaft 210. As described in further detail below, the retraction and extension of the actuation shaft 214 provides control of the end effector assembly 300 coupled to the distal end 218 of the shaft assembly 200.

Figure 5:
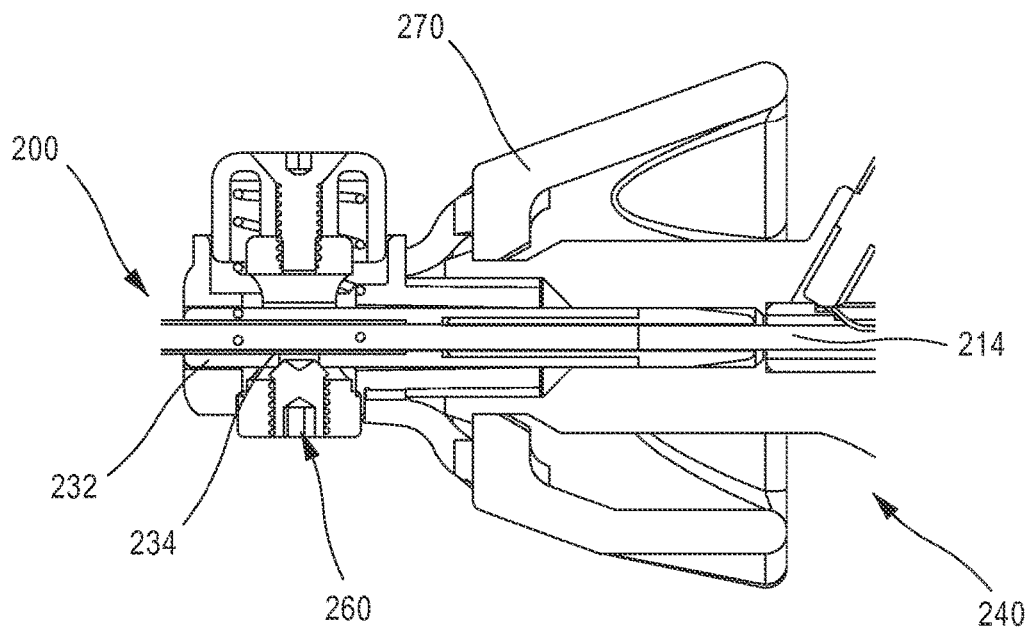
FIG. 5 is an enlarged view of portions of the instrument handle to illustrate a method of coupling a proximal portion of a shaft assembly to an instrument handle, in accordance with aspects of the present disclosure.

To couple the shaft assembly 200 to the instrument handle 240 for use during a procedure, the outer shaft 210 with actuation shaft 214 and lock ball 236 extending therefrom are inserted through a shaft receptacle 256 of the instrument handle 240. As shown in the enlarged view of FIG. 5, the shaft assembly 200 may be inserted until a spring biased locking setscrew 260 engages the shaft lock receptacle 234 to secure the shaft assembly 200 to the instrument handle 240. The setscrew 260 may be part of a rotation knob unit 270 mounted to the main body portion 242 of the instrument handle 240. Electronic circuitry may be provided, including mounted control buttons, for example, and configured into the instrument handle 240 for controlled rotation of the knob unit 270, which provides controlled rotation of the shaft assembly 200 and the end effector assembly 300 coupled thereto.

Figure 6:
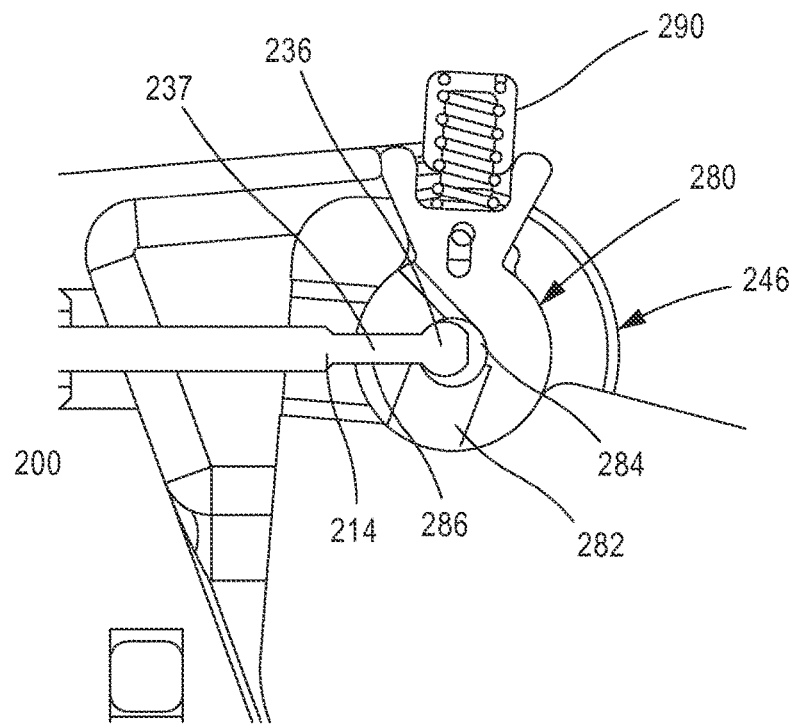
FIG. 6 is an enlarged view of portions of the instrument handle to illustrate a method of coupling a proximal portion of a shaft assembly to an instrument handle, in accordance with aspects of the present disclosure.

As shown in the enlarged view of FIG. 6, a shaft securement assembly 280 may be used to capture the lock ball 236 of the actuation shaft 214. For example, the shaft securement assembly 280 may be rotationally mounted to a distal portion of the thumb lever 246 such that a lock ball receiving channel 282 may axially align with the axis of the actuation shaft 214. The lock ball receiving channel 282 receives the lock ball 236 until the lock ball 236 is received into a main bearing chamber 284. The shaft securement assembly 280 has a lock channel 286 of reduced dimension from that of the diameter of the lock ball receiving channel 282. Accordingly, a reduced diameter section 237 of the acuation shaft 214 extending distally from the lock ball 236 may slide through the lock channel 286 as the shaft securement assembly 280 rotates. Thus, when the lock ball 236 is situated in the main bearing chamber 284, rotation of the securement assembly 280 rotates the lock ball receiving channel 282 out of alignment with the central axis of the actuation shaft 214. Because the diameter of the lock ball 236 is wider than a transverse dimension the lock channel 286, the lock ball 236 is held secure in the bearing chamber 284 while the reduced diameter section 237 slides through the lock channel 286 and the actuation shaft 214 is secured to the shaft securement assembly 280. A spring loaded button 290 may be used to prevent or allow rotation of the shaft securement assembly 280 to prevent or allow release of the actuation shaft 214 from the shaft securement assembly 280.

With the actuation shaft 214 thus secured to the thumb lever 246 via the shaft securement assembly 280, an application or release of pressure on the thumb lever 246 rotates the thumb lever 246 in a manner that permits a precisely controlled retraction or extension of the actuation shaft 214 through the outer shaft 210 for controlled actuation of the end effector assembly 300 as described in additional detail below. The controlled actuation may be manual, for increased tactile awareness for example, and/or controlled via electronic circuitry configured into the instrument handle 240.

Figure 7:
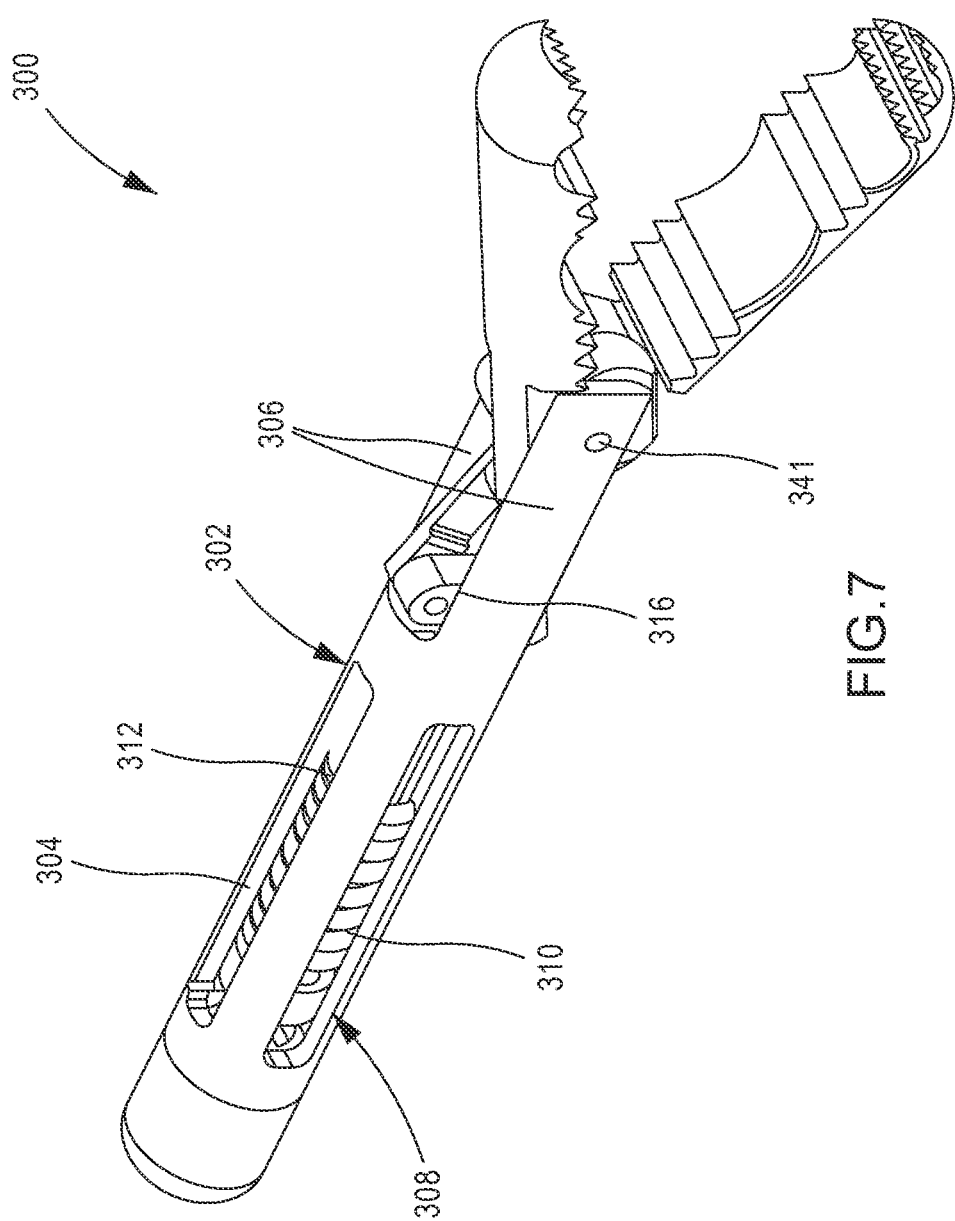
FIG. 7 is a perspective view of an end effector assembly, in accordance with aspects of the present disclosure.
Figure 8:
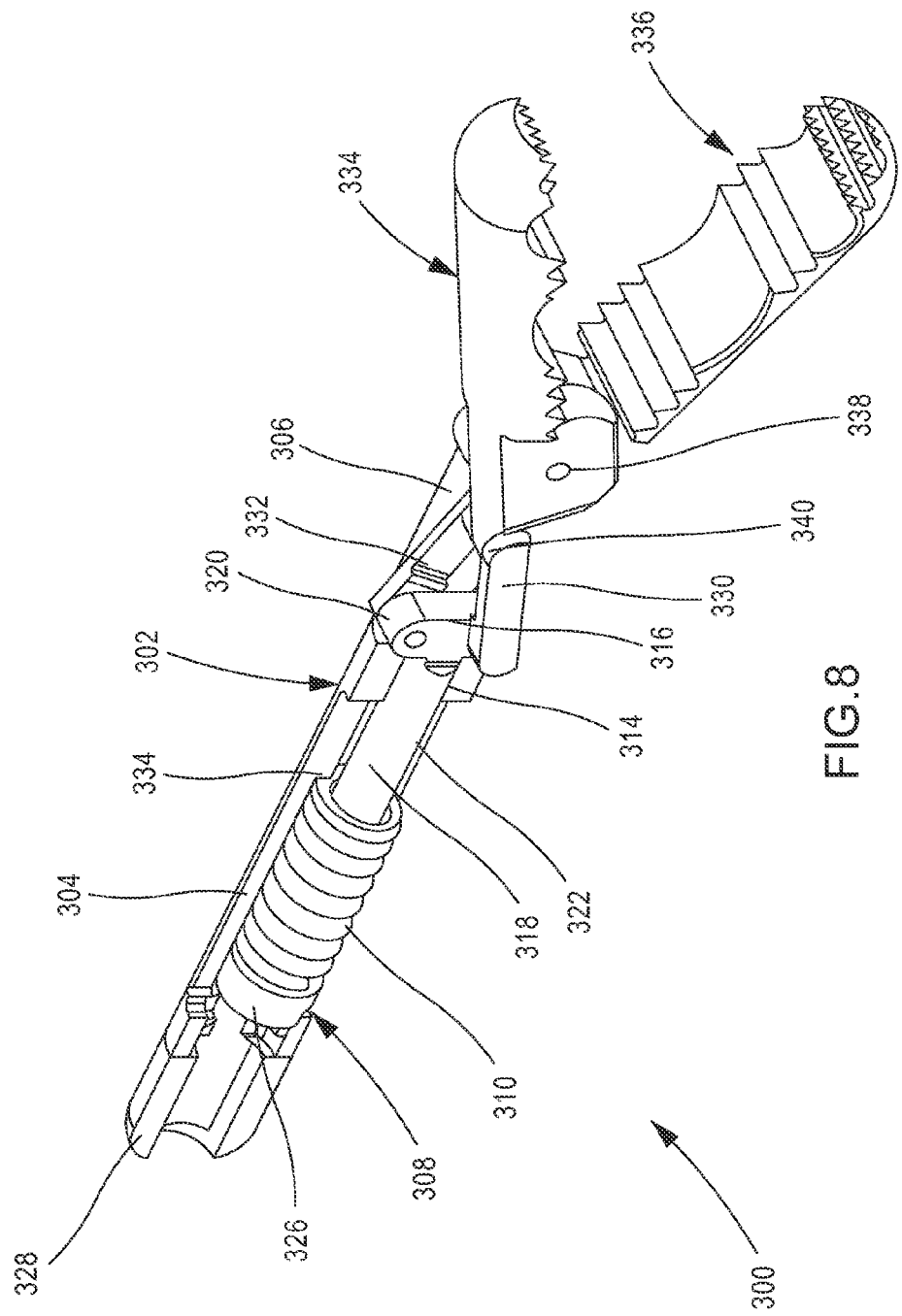
FIG. 8 is a perspective view of the end effector assembly shown in FIG. 7 with a portion cutaway to reveal internal components of the assembly, in accordance with aspects of the present disclosure.
Figure 9:
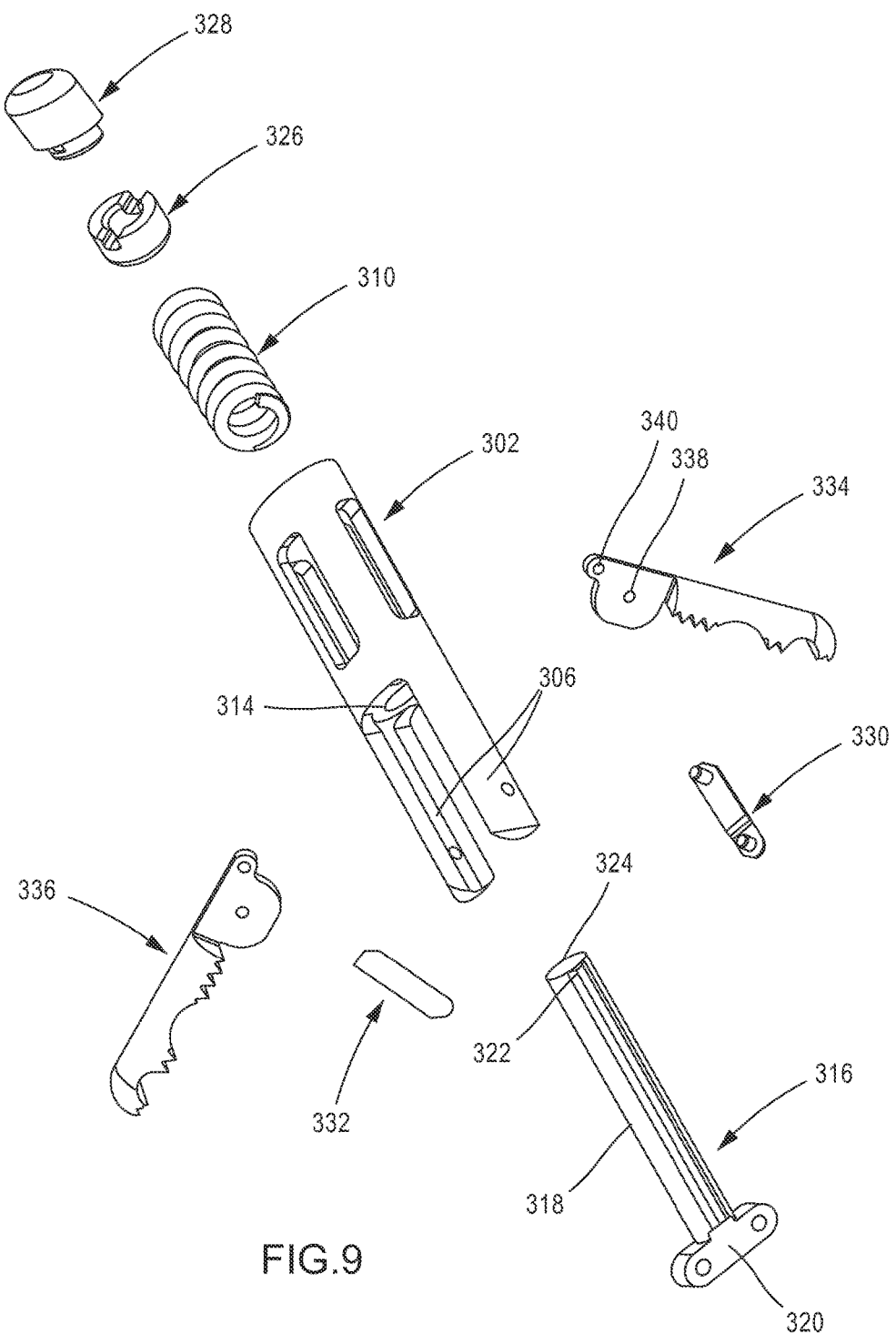
FIG. 9 is a exploded view of the end effector assembly to illustrate various component parts, in accordance with aspects of the present disclosure.

FIG. 7 is a perspective view of an end effector assembly 300 in accordance with aspects of the present invention. FIG. 8 is cutaway view of the end effector assembly shown in FIG. 7 to illustrate the assembly of the components of the end effector assembly 300. FIG. 9 is an exploded view of the component parts shown in FIGS. 7 and 8.

The end effector assembly 300 may be a 5 mm working system for actuating the opening and closing of a multiple jaw configuration for use as scissors, graspers, dissectors, and clip appliers, for example. The end effector assembly 300 may include a hinge tube 302 that serves as a primary frame component for the end effector assembly 300. The hinge tube 302 may be configured with a substantially hollow portion 304 arranged toward a proximal end and two symmetrical arms 306 extending longitudinally toward a distal end. The hollow portion 304 may be substantially open at the proximal end and define a chamber 308 having a first internal diameter. The chamber 308 may be configured to house a compression spring 310 therein. A detent or step 312 may be provided to seat one end of the compression spring 310, wherein the step 312 may be formed by a reduction of the first internal diameter to a second internal diameter. The distal end of the hollow portion 304 may be substantially closed except that a rod opening 314 is provided that functions as a bearing surface for slidably supporting a push rod 316.

As shown in FIGS. 8 and 9, the push rod 316 may include a substantially cylindrical rod 318 integrally formed with or joined to an actuator head 320. The actuator head 320 may be an oblongated portion that extends transverse to a longitudinal center axis of the cylindrical rod 318. The cylindrical rod 318 may be keyed, for example, by including a protrusion 322 and/or a flat portion 324 extending the longitudinal length of the rod 318. The rod opening 314 may be dimensioned to correspond to the keyed configuration of the protrusion 322 and flat portion 324. Thus, when the push rod 316 is mounted as shown in FIG. 8, wherein the cylindrical rod 318 extends through the rod opening 314, the actuator head 320 is situated between the symmetrical arms 306 and prevented from independent rotation separate from rotation of the hinge tube 302.

With the cylindrical rod 318 of the push rod 316 extending through rod opening 314 into the chamber 308, the compression spring 310 may be concentrically arranged around the cylindrical rod 318 with one end of the spring 310 seated against the step 312 and the other end seated against a spring retainer 326. The spring retainer 326 may be mounted onto the free end of the cylindrical rod 318 so that the compression spring 310 biases the push rod 316 toward the proximal end of the assembly 300. An end cap 328 may be provided to seal the open end of the hinge tube 302. The end cap 328 may serve as a stop against the unrestrained axial movement of the spring retainer 326 caused by the compression spring 310. Likewise, the distal end of the hollow portion 304, where the cylindrical rod 318 first enters through the rod opening 314 when extending toward the chamber 308, may serve as a stop against axial movement in a proximal direction of the push rod 316 as a result of the compression spring 310. As shown in FIGS. 7 and 8, for example, the actuator head 320 may seat against the distal end of the hollow portion 304 when the compression spring 310 is in a maximally extended position. Any pressure exerted against a proximal side of the spring retainer 326, i.e., in a direction toward the distal end of the assembly 300, forces the spring retainer 326 to slide forward through the chamber 308 against the compression force of the spring 310. As the spring retainer 326 slides forward, the push rod 316 is also forced to slide forward.

Rotatably attached to the actuator head 320 of the push rod 316 is an upper link 330 and a lower link 332. The upper link 330 may be rotatably attached to an upper jaw 334 and the lower link 332 may be rotatably attached to a lower jaw 336. Although defined herein as an upper jaw 334 and a lower jaw 336, for example, both jaws may be configured exactly the same, one jaw being arranged and mounted in inverted and opposing fashion from the other jaw. Accordingly, each of the upper and lower jaws 334 and 336 may have a hinge mount 338 (see FIGS. 8 and 9) and a pin mount 340. A hinge pin 341 (see FIG. 7) may be used to rotatably mount the upper and lower jaws 334 and 336 between the symmetrical arms 306 in an opposing configuration. The pin mount 340 may be used to rotatably mount a rear portion of the upper and lower jaws 334 and 336 to respective upper and lower links 330 and 332. The upper and lower jaws 334 and 336 may have structural features, such as ridges or blades, for performing a specific function during a procedure.

Figure 10:
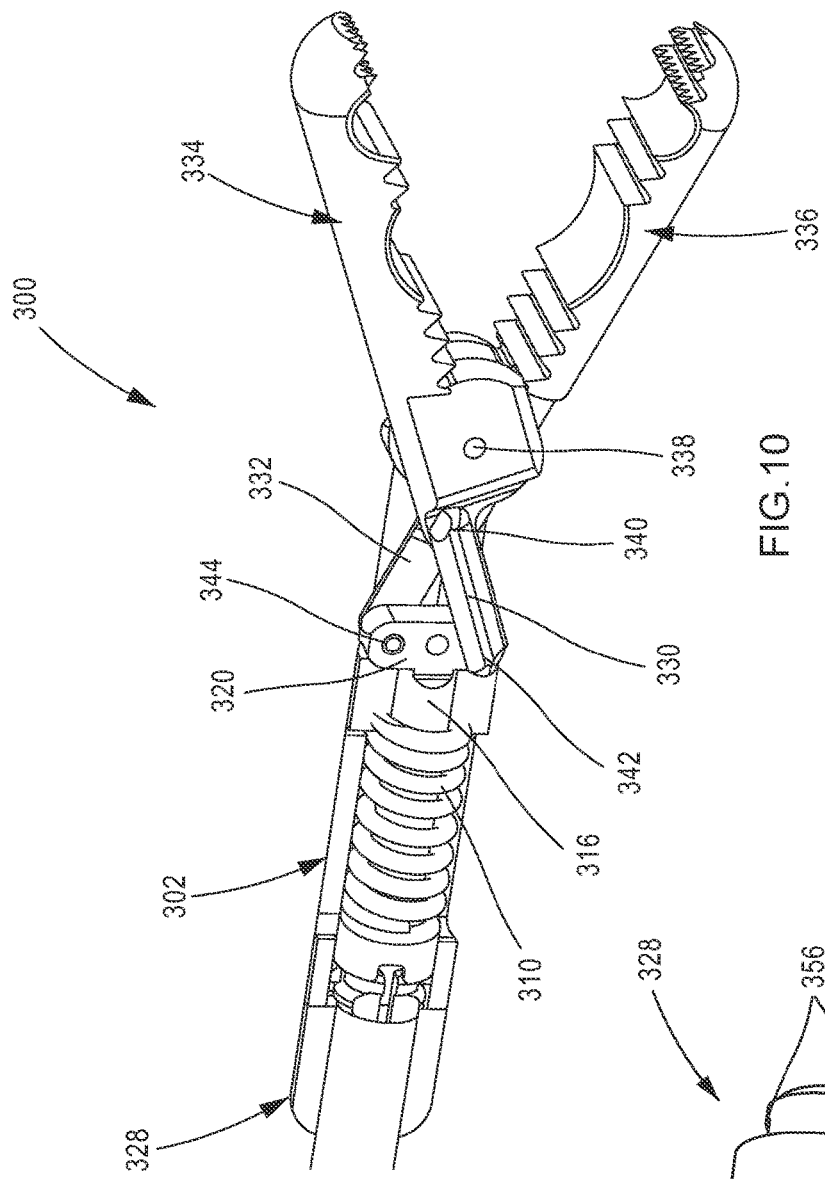
FIG. 10 is a perspective view of the end effector actuation system with a portion cutaway to reveal internal components of the system, in accordance with aspects of the present disclosure.

As shown in FIG. 10, the upper and lower links 330 and 332 may be each attached at one end to the respective pin mounts 340 on the upper and lower jaws 334 and 336. The other end of each of the upper and lower links 330 and 332 may be rotatably mounted to the actuator head 320 of the push rod 316. For example, the upper link 330 may be attached to a lower rod mount 342 and the lower link 332 may be attached to an upper rod mount 344 of the actuator head 320. The dimensions of the links 330 and 332 and the crisscrossed nature of their mounting is such that the jaws are normally biased into an open position when the compression spring 310 and the spring retainer 326 are fully extended, i.e., when the assembly 300 is in a non-actuated, rest position. However, when an applied force, such as that from the actuation shaft 214 acting on the spring retainer 326, forces the push rod 316 forward, a reverse torque is simultaneously created about the hinge mount 338 on each of the upper and lower jaws 334 and 336. The applied force translated through the upper and lower links 330 and 332 causes the upper and lower jaws 334 and 336 to rotate towards a closed position as the push rod 316 translates forward axially. In this manner, the upper and lower jaws 334 and 336 may be forced closed to grasp, dissect, manipulate and/or hold a target anatomical feature as required for performing a particular medical procedure.

Figure 11:
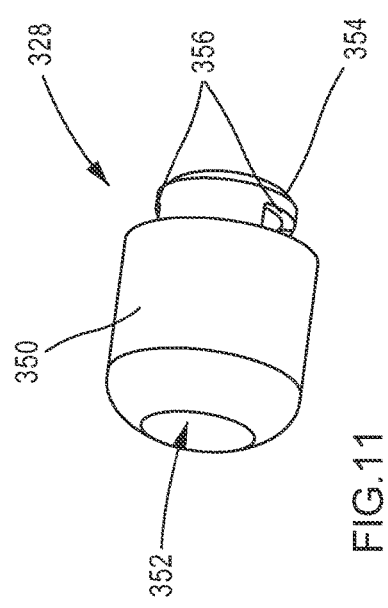
FIG. 11 is an enlarged perspective view of an end cap for use with an end effector assembly, in accordance with aspects of the present disclosure.

For connecting the shaft assembly 200 to the end effector assembly 300, FIG. 11 illustrates an enlarged view of the end cap 328. The end cap 328 may be formed to be compression fit, for example, into the open end of the hinge tube 302. The end cap 328 may have a primary housing 350 with a cap opening 352 for receiving the shaft assembly 200 therethrough. For example, the cap opening 352 may be formed to be approximately 3 mm if the outer shaft 210 of the of the shaft assembly 200 has an outer diameter of 3 mm. The primary housing 350 may be formed to have an outside diameter equal to an outside diameter of the hinge tube 302. An insertion flange 354 may be integrally formed to extend from the primary housing 350. The insertion flange 354 may have a reduced outside diameter that is the same or slightly larger than the inside diameter of the open end of the hollow portion 304 of the hinge tube 302. The insertion flange 354 may thus be received into the open end of the hinge tube 302 until the primary housing 350 abuts the hinge tube 302. The insertion flange 354 may be formed with one or more shaft retention pockets 356. The shaft retention pockets 356 may be dimensioned, for example, to correspond to the dimensions of the locking bosses 224 located on the outer shaft 210 of the shaft assembly 200.

FIGS. 12-15 illustrate a method of connecting the shaft assembly 200 to an end effector assembly 300 in accordance with aspects of the present invention. FIG. 12 illustrates the shaft assembly 200 with the actuation shaft 214 in a neutral position, wherein the actuation shaft 214 extends entirely or substantially through the lumen 212. As shown in FIG. 13, the actuation shaft may be drawn back into the lumen 212. The absence of the actuation shaft 214 in the lumen between the flexing arms 226 allows the flexing arms 226 to be compressed toward one another into the space provided by the flexing slits 220, permitting the distal end 218 of the shaft 210 to assume a smaller diameter than the diameter of the shaft 210 that exists when the flexing arms 226 are uncompressed. Accordingly, as shown in FIGS. 14-15, the shaft assembly 200 may be inserted into the cap opening 352 of the end cap 328. As the shaft assembly is inserted, the distal end 218 of the outer shaft 210 compresses so that the locking bosses 224 may pass into the primary housing 350 of the end cap 328. The shaft assembly 200 may be slid forward into the end cap 328 until upper and lower locking bosses 224 align with the shaft retention pockets 356 of the end cap 328. Once aligned, the flexing arms 226 may be free to expand so that the locking bosses 224 become seated in the shaft retention pockets 356 provided in the end cap 328.

As shown in FIG. 16, with the locking bosses 224 thus seated in the shaft retention pockets 356 of the end cap 328, the actuation shaft 214 may be permitted to return forward to the neutral position. With the actuation shaft 214 thus extending again through the lumen 212, the flexing arms 226 are unable to be compressed and the shaft assembly 200 is locked in coupled arrangement with the end effector assembly 300. The actuation shaft 214 may now be actuated to move further inward and/or back outward toward the neutral position to respectively apply or release pressure against the spring retainer 326, actuating the jaws to open and close as described above. In addition, with the locking bosses 224 seated in locked relationship with the retention pockets 356 of the end cap 328, rotation of the outer shaft 210 will result in rotation of the end effector assembly 300.

Figure 17:
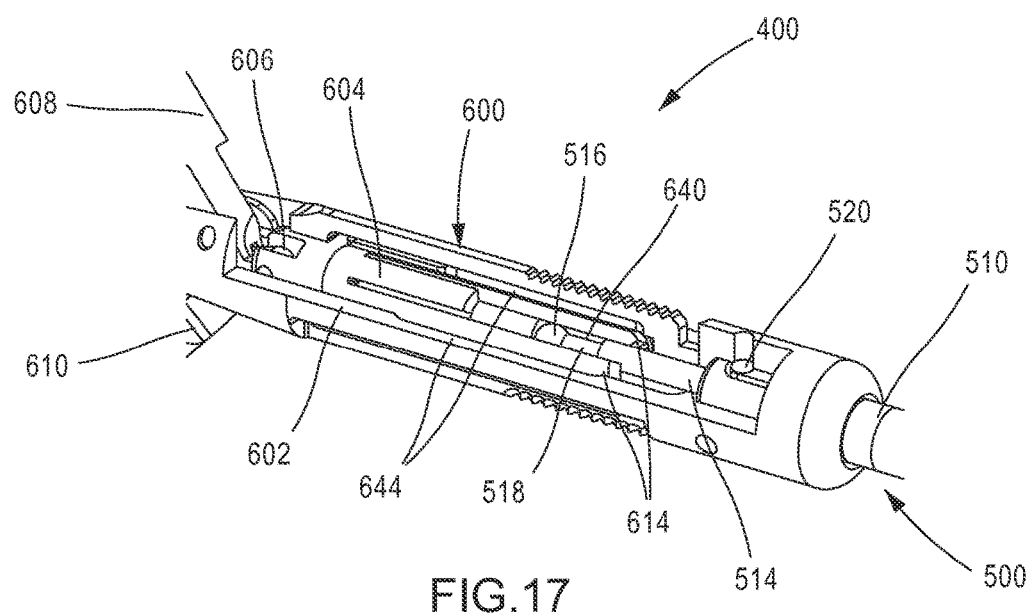
FIG. 17 is a perspective view of another end effector actuation system comprising a shaft assembly and end effector assembly, in accordance with aspects of the present disclosure.

FIG. 17 is a perspective view illustrating an end effector actuation system 400 according to an embodiment of the present disclosure. The actuation system 400 may include a shaft assembly 500 and an end effector assembly 600 coupled together as described below, for example, in order to articulate the end effector assembly 600 manually or robotically in a manner that provides a specific function or capability during a minimally invasive medical procedure.

Figure 18:
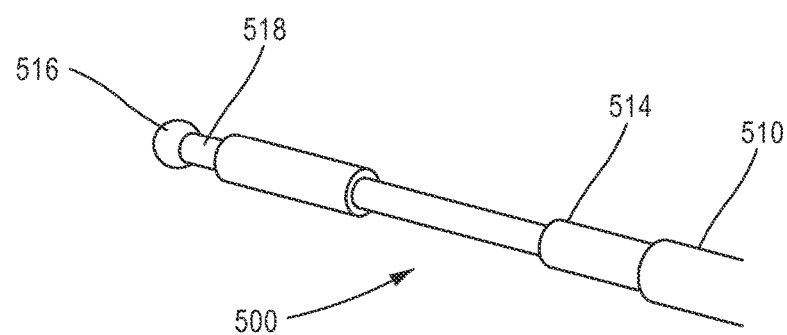
FIG. 18 is a perspective view of a shaft assembly, in accordance with aspects of the present disclosure.

The shaft assembly 500 may include an outer shaft 510 made of a high-quality, durable material, such as stainless steel or a temperature resistant plastic. The outer shaft 510 may be configured to have an outside diameter of approximately 3 mm for coupling with 5 mm end-effector assemblies, for example. The outer shaft 510 may be generally straight and configured with an inner lumen for slidably accommodating an actuation shaft 514. As shown enlarged in FIG. 18, the actuation shaft 514 may include a ball end 516 and at least one channel groove region 518 having a reduced diameter from the shaft diameter, the shaft diameter being substantially equal to an inner diameter of the outer shaft 510. Referring back to FIG. 17, the outer shaft 510 may be provided with a locking mechanism 520, such as a snap-fit detent or a spring-loaded ball lock, for example, for releasably coupling the outer shaft 510 to the end effector assembly 600.

As shown in FIG. 17, the effector assembly 600 may include a substantially cylindrical clevis rod 602 for housing a tip collet 604. The tip collet may be rotatably attached to one end of a link 606 that is coupled at the other end to both an upper jaw 608 and a lower jaw 610. The upper and lower jaws 608 and 610 are rotatably coupled to the link 606 and configured to open and close as the tip collet 604 moves forward or backward through an interior portion of the clevis rod 602.

Figure 19:
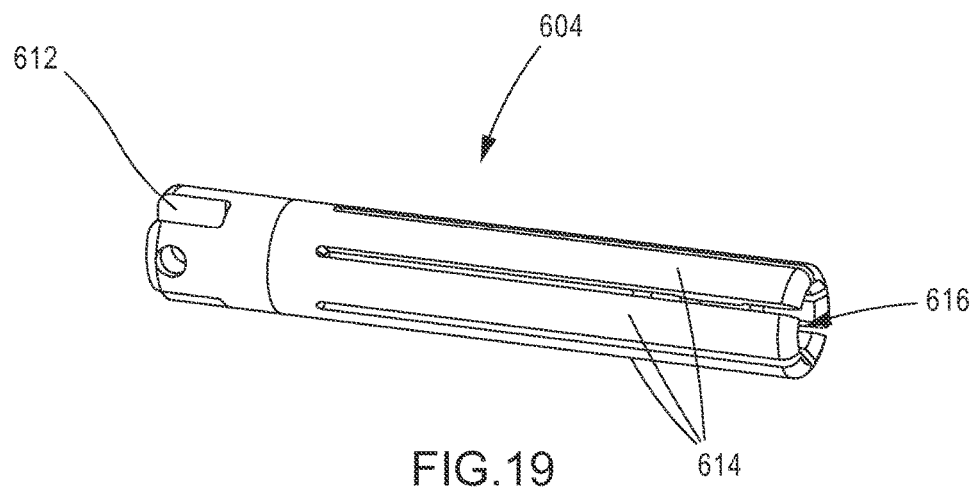
FIG. 19 is a perspective view of a tip collet, in accordance with aspects of the present disclosure.

As shown in the enlarged view of FIG. 19, the tip collet 604 has hinge channel 612 for rotatably coupling one end of the link 606 to the tip collet 604. The tip collet 604 is configured to have a plurality of collet petals 614 that form a collet opening 616 for receiving the ball end 516 of the actuation shaft 514.

Figure 20:
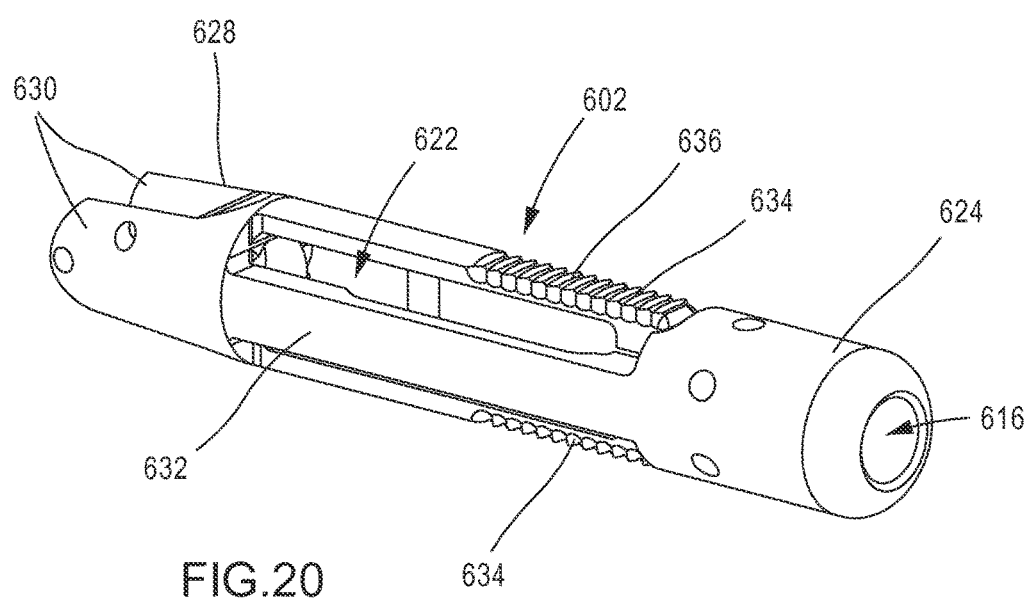
FIG. 20 is a perspective view of a clevis rod, in accordance with aspects of the present disclosure.

As shown in the enlarged view of FIG. 20, the clevis rod 602 has an interior portion 622 for housing the tip collet 604. A proximal end portion 624 has a clevis receiving hole 626 for receiving the shaft assembly 500 when coupling the end effector assembly 600 onto the shaft assembly 500. A distal end portion 628 of the clevis rod 602 may be formed with mounting arms 630 that have various through-holes provided for hinge pins to be mounted for support and actuation of the jaws at the distal end 628 of the clevis rod 602. The distal end portion 628 and the proximal end portion 624 of the clevis rod 602 may be joined by one or more main longitudinal support beams 632. One or more flexible grip beams 634 may be radially spaced in between the support beams 632 to extend longitudinally from the distal end portion 628 toward the proximal end portion 624. The flexible grip beams 634 do not connect to the proximal end portion 624 but extend in cantilevered fashion from the distal end portion 628. Finger grip pads 636 may be provided at the cantilevered ends of the flexible grip beams 634.

Referring back to FIG. 17, to connect the shaft assembly 500 to the end effector 600, the outer shaft 510 is first extended throught the clevis receiving hole 626 until being releasably secured. The actuation shaft 514 may then be extended so that the ball end 516 of the shaft 514 enters the collet opening 616. One of the collet petals 614 has been cutaway in FIG. 17 to further illustrate the coupling concept. Each collet petal 614 has a locking boss region 640 that is a protruding area formed to mate with the channel groove region 518 of the actuation shaft 514. As the ball end 516 of the shaft 514 meets the locking boss region 640 of the tip collet 604, the tip collet 604 is forced into a forward position in the clevis rod 602. The support beams 632 and grip beams 634 are formed to provide a clevis void region 644. The clevis void region 644 is an area of increased internal diameter that creates a gap wide enough for the collet petals 614 to expand outward when the tip collet 604 is in the forward position. With the collet petals 614 able to expand into the clevis void region 644, continued forward movement of the actuation shaft 514 forces the ball end 516 to pass the locking boss region 640. The collet petals 614 expand until the ball end 516 passes the locking boss region 640. The collet petals 614 may then snap back into place with the locking boss regions 640 safely secured in the channel groove region 518 of the actuation shaft 514.

Figure 21:
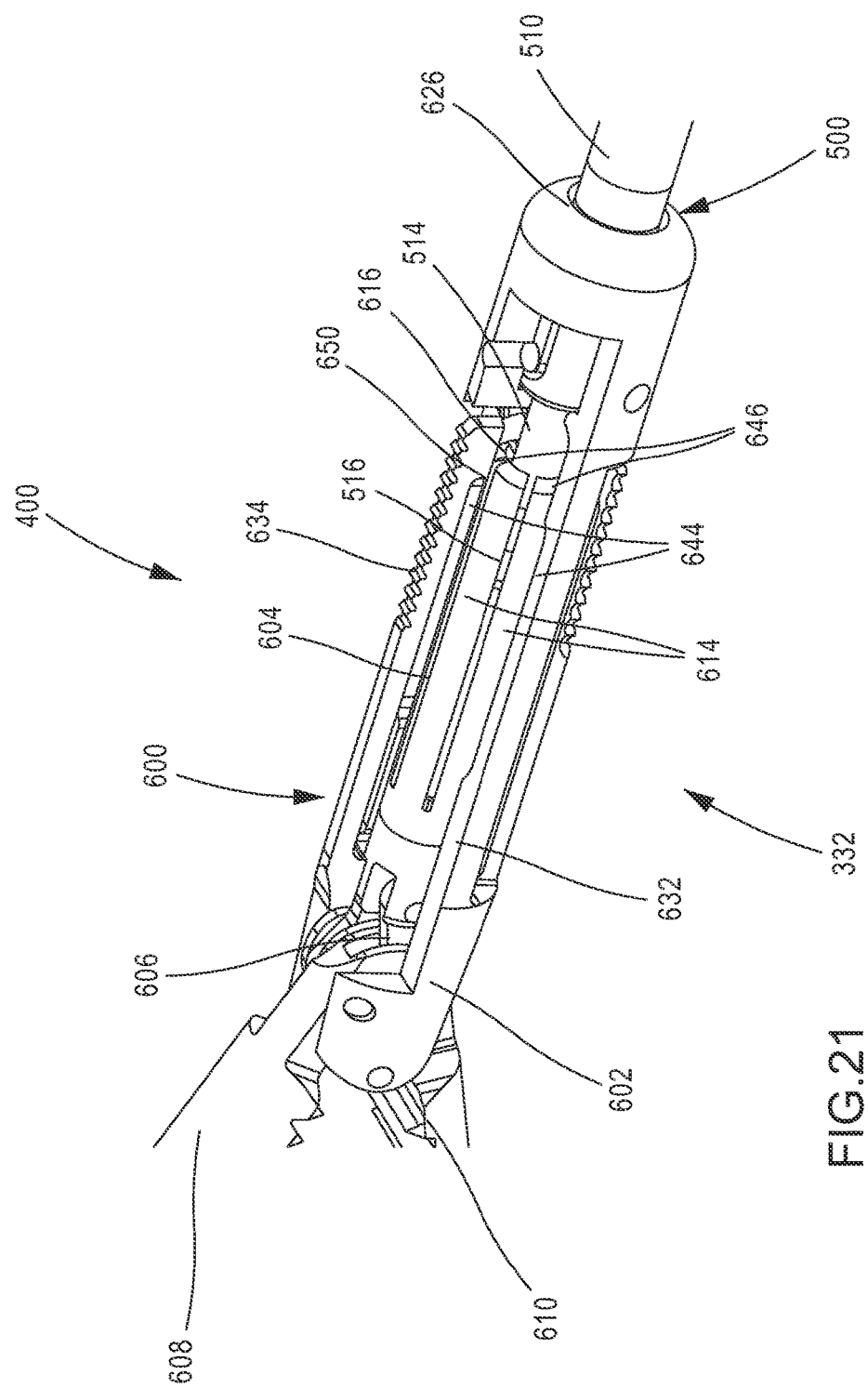
FIG. 21 is a perspective view of the end effector actuation system of FIG. 17 in a state of use, in accordance with aspects of the present disclosure.

As shown in FIG. 21, with the ball end 516 secured in the tip collet 604, the actuation shaft 514 may be pulled in a proximal direction so that the ends of the collet petals 614 are forced into a clevis restriction area 646. The clevis restriction area is an area of decreased internal diameter formed on the support beams 632 and the grip beams 634 that restricts expansion of the collet petals 614. Thus, as the actuation shaft 514 is pulled proximally, the collet petals 614 are unable to expand preventing release of the ball end 516 from the tip collet 604. Continued proximal movement of the actuation shaft 514 forces closure of the upper and lower jaws 608 and 610.

To release the end effector assembly 600, the actuation shaft 514 may be pushed into the forward position until the collet petals 614 are released from the clevis restriction area 646 into the clevis void region 644. Pressure may then be applied to the cantilevered grip beams 634, forcing the free ends of the grip beams 634 to flex inward. Detents 650 provided on an inner surface of the grip beams 634 are formed as stops to prevent proximal movement of the tip collet 604 when the grip beams 634 are flexed inward. Accordingly, the actuation shaft 514 may then be actuated to move proximally. The collet petals 614 are prevented by the detents 650 from entering the clevis restriction area 646 and instead remain in the clevis void region 644. The collet petals 614 may thus expand into the clevis void region 644 so that the ball end 516 of the actuation shaft 514 may move proximally past the locking boss region 640, decoupling the actuation shaft 514 from the tip collet 604. The outer shaft 510 may then be disengaged from the clevis rod 602 and the end effector assembly 600 disengaged from the shaft assembly 500.

Figure 22:
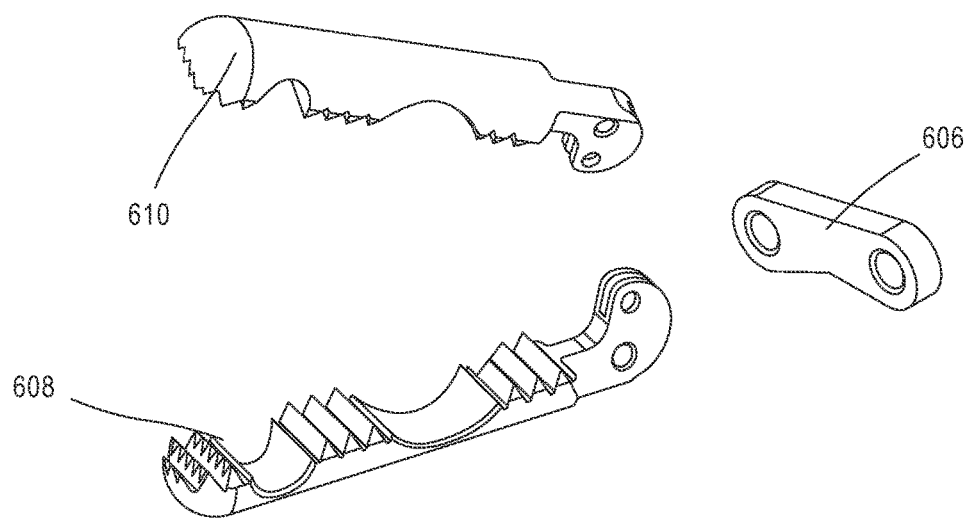
FIG. 22 is an exploded view to illustrate component parts of a jaw assembly for use with an end effector assembly, in accordance with aspects of the present disclosure.

FIG. 22 illustrates an exploded view of the component parts forming the jaw assembly, namely the upper jaw 608, the lower jaw 610, and the link 606. The jaw assembly of FIG. 22 may be common to the various embodiements depicted in FIGS. 17-21 as well as those depicted in the following FIGS. 23-35.

FIG. 23 is a perspective view illustrating an end effector actuation system 700 according to an embodiment of the present disclosure. The actuation system 700 may include a shaft assembly 800 and an end effector assembly 900 coupled together as described below, for example, in order to articulate the end effector assembly 900 manually or robotically in a manner that provides a specific function or capability during a minimally invasive medical procedure.

The shaft assembly 800 may include an outer shaft 810 made of a high-quality, durable material, such as stainless steel or a temperature resistant plastic. The outer shaft 810 may be configured to have an outside diameter of approximately 3 mm for coupling with 5 mm end-effector assemblies, for example. The outer shaft 810 may be generally straight and configured with an inner lumen for slidably accommodating an actuation shaft 814. As shown in the enlarged view of FIG. 24, the actuation shaft 814 may include an frustoconical tip end 816. The outer shaft 810 may be provided with a locking mechanism, such as a snap-fit detent or a spring-loaded ball lock, for example, for releasably coupling the outer shaft 810 to the end effector assembly 900.

As shown in FIG. 23, the end effector assembly 900 may include a clevis 902 for securing a rod tip connector 904. The rod tip connector 904 may be rotatably attached to one end of a link 906 that is coupled at the other end to both an upper jaw 908 and a lower jaw 910. The upper and lower jaws 908 and 910 are rotatably coupled to the link 906 and configured to open and close as the rod tip connector 904 moves forward or backward through an interior portion of the clevis 902.

Figure 25:
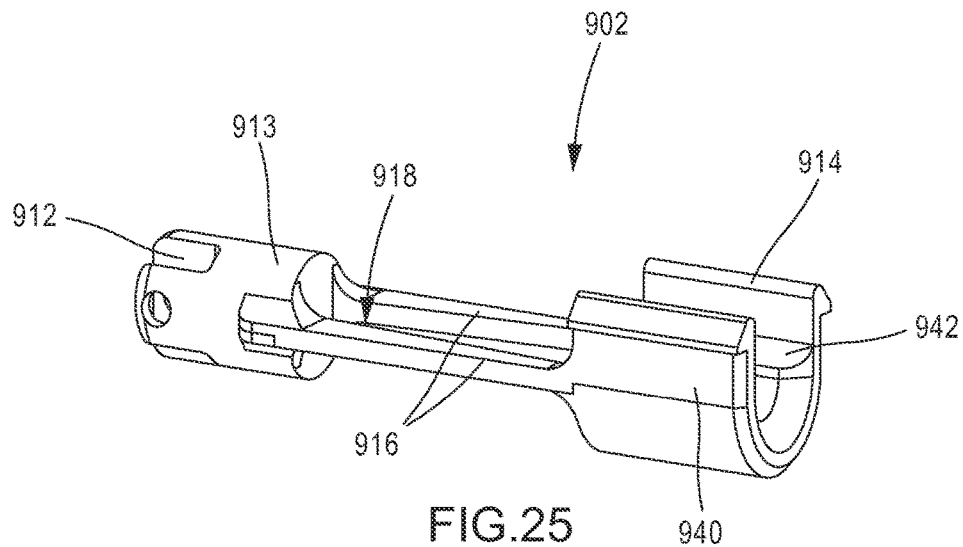
FIG. 25 is a perspective view of a rod tip connector, in accordance with aspects of the present disclosure.

As shown in the enlarged view of FIG. 25, the rod tip connector 904 may include a hinge channel 912 at a distal end 913 for rotatably coupling one end of the link 906 to the rod tip connector 904. A proximal receptacle portion 914 includes two flexing beams 916 arranged towards a centerline and a tip pocket 918 for cradling the tip end 816.

Figure 26:
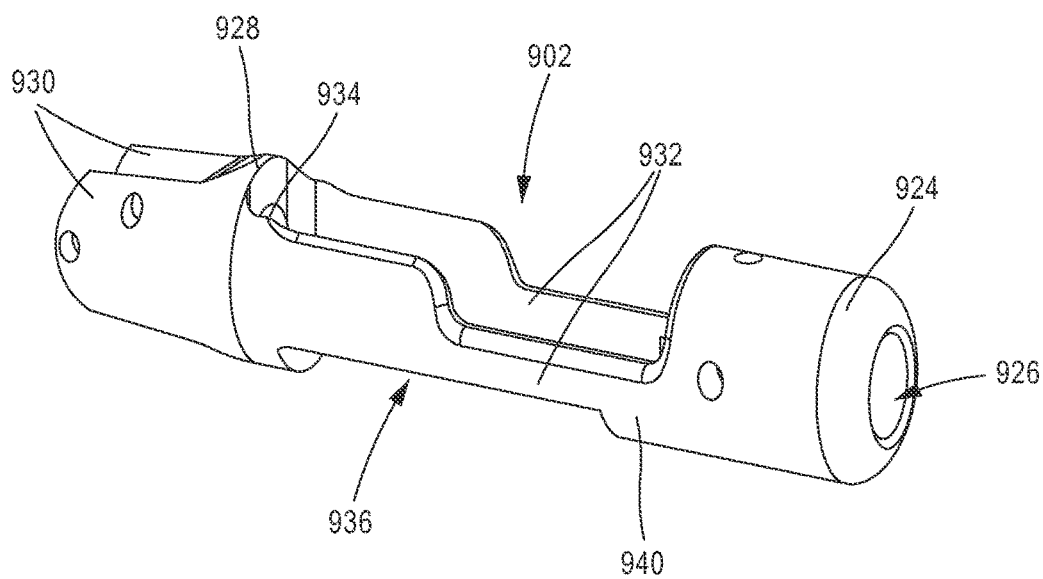
FIG. 26 is a perspective view of a clevis, in accordance with aspects of the present disclosure.
Figure 27:
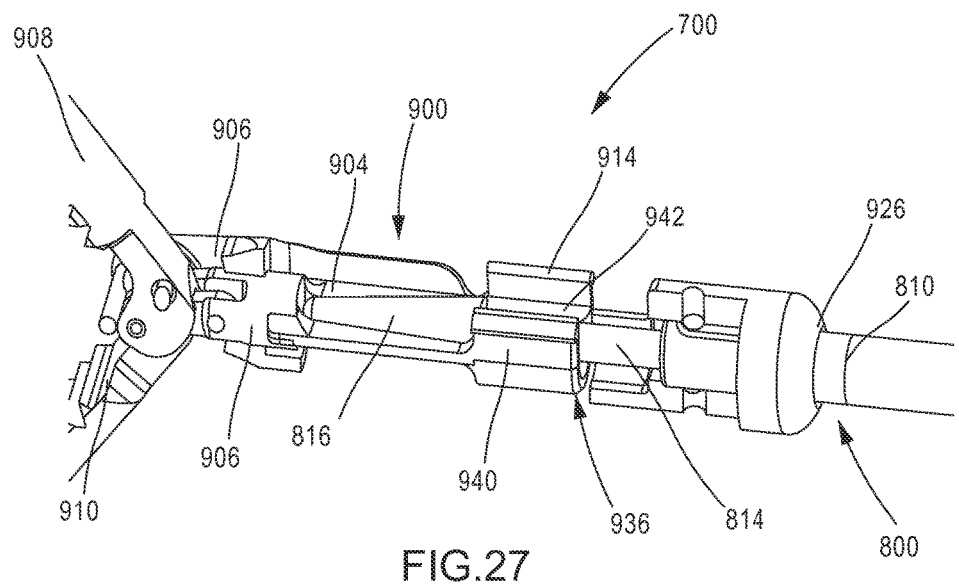
FIG. 27 is a perspective view of the end effector actuation system of FIG. 23 in a state of use, in accordance with aspects of the present disclosure.

As shown in the enlarged view of FIG. 26, the clevis 902 may include a proximal end portion 924 with a clevis receiving hole 926 for receiving the shaft assembly 800 when coupling the end effector assembly 900 onto the shaft assembly 800. A distal end portion 928 of the clevis 902 may be formed with mounting arms 930 that have various through-holes provided for hinge pins to be mounted for support and actuation of the jaws at the distal end 928 of the clevis 902. The distal end portion 928 and the proximal end portion 924 of the clevis 902 may be joined by one or more main longitudinal support beams 932. A tip connector receiving through-hole 934 may be provided through the distal end portion 928 along a central axis of the clevis 902. An open clevis void area 936 is formed by the absence of any structure connecting the support beams 932 along a longitudinal lower portion of the clevis 902 and a clevis restriction area 938 is formed toward the proximal end 924 of the clevis 902 where a cylindrical lower wall extends forward from the proximal end 924 a predetermined distance towards the distal end portion 928, closing that lower portion of the clevis 902 between the support beams 932.

Referring back to FIG. 23, the rod tip connector 904 is mounted into the clevis 902 so that the distal end 913 is received through receiving through-hole 934. To connect the shaft assembly 800 to the end effector 900, the outer shaft 810 is first extended throught the clevis receiving hole 926 until it is releasably secured. The actuation shaft 814 may then be extended so that the tip end 816 of the shaft 814 is pushed into the rod tip connector 904. The proximal receptacle portion 914 of the rod tip connector 904 is configured to flex downward through the clevis void area 936, as shown in the cutaway view shown in FIG. 27. Each side wall 940 of the receptacle portion 914 has a locking boss 942 that is a protruding area formed to lock the tip end 816 into the rod tip connector 904 upon engagement. An audible click may be heard, for example, once the tip end 816 passes by the locking bosses 942 and the receptacle portion 914 flexes back into place with the locking bosses 942 surrounding the actuation shaft 814.

Figure 28:
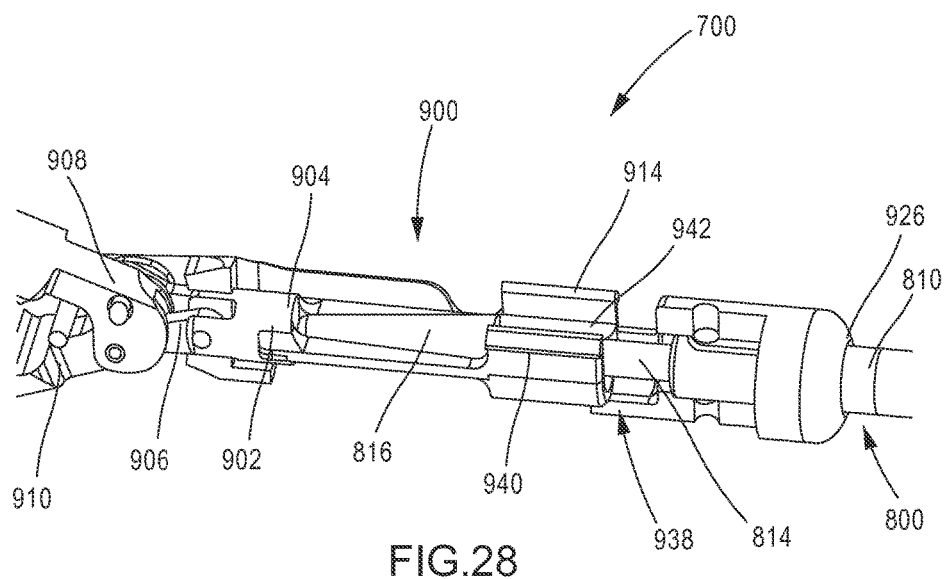
FIG. 28 is a perspective view of the end effector actuation system of FIG. 23 in another state of use, in accordance with aspects of the present disclosure.

As shown in FIG. 28, with the tip end 816 secured in the tip connector 904, the actuation shaft 814 may be pulled in a proximal direction so that the receptacle portion 914 is forced into the clevis restriction area 938. The clevis restriction area 938 prevents the downward or outward flexing of the side walls 940 and thus the locking bosses 942 keep the tip end 816 locked in the tip connector 904. Continued proximal movement of the actuation shaft 814 forces closure of the upper and lower jaws 908 and 910.

To release the end effector assembly 900, the actuation shaft 814 may be pushed into the forward position until the receptacle portion 914 is released from the clevis restriction area 938 into the clevis void area 936. Pressure may then be applied to the receptacle portion 914 in order to push down and/or flex out the side walls 940 through the clevis void area 936 so that the tip end 816 of the actuation shaft 814 may move proximally past the locking bosses 942, decoupling the actuation shaft 814 from the tip connector 904. The outer shaft 810 may then be disengaged from the clevis 902 and the end effector assembly 900 disengaged from the shaft assembly 800.

FIG. 29 is a perspective view illustrating an end effector actuation system 1000 according to an embodiment of the present disclosure. The actuation system 1000 may include a shaft assembly 1100 and an end effector assembly 1200 coupled together as described below, for example, in order to articulate the end effector assembly 1200 manually or robotically in a manner that provides a specific function or capability during a minimally invasive medical procedure.

The shaft assembly 1100 may include an outer shaft 1110 made of a high-quality, durable material, such as stainless steel or a temperature resistant plastic. The outer shaft 1110 may be configured to have an outside diameter of approximately 3 mm for coupling with 5 mm end-effector assemblies, for example. The outer shaft 1110 may be generally straight and configured with an inner lumen for slidably accommodating an actuation shaft 1114. As shown in the enlarged view of FIG. 30, the actuation shaft 1114 may include an tip end 1116 and at least one recessed channel portion 1118. The outer shaft 1110 may be provided with a locking mechanism, such as a snap-fit detent or a spring-loaded ball lock, for example, for releasably coupling the outer shaft 1110 to the end effector assembly 1200.

As shown in FIG. 29, the end effector assembly 1200 may include a clevis 1202 for securing a rod tip connector assembly 1204. The rod tip connector assembly 1204 may be rotatably attached to one end of a link 1206 that is coupled at the other end to both an upper jaw 1208 and a lower jaw 1210. The upper and lower jaws 1208 and 1210 are rotatably coupled to the link 1206 and configured to open and close as the rod tip connector assembly 1204 moves forward or backward through an interior portion of the clevis 1202.

Figure 31:
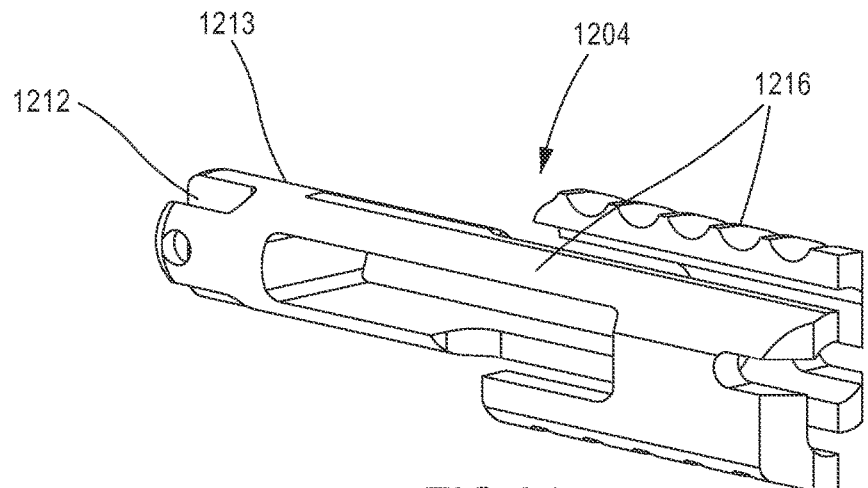
FIG. 31 is a perspective view of a rod tip connector assembly, in accordance with aspects of the present disclosure.
Figure 32:
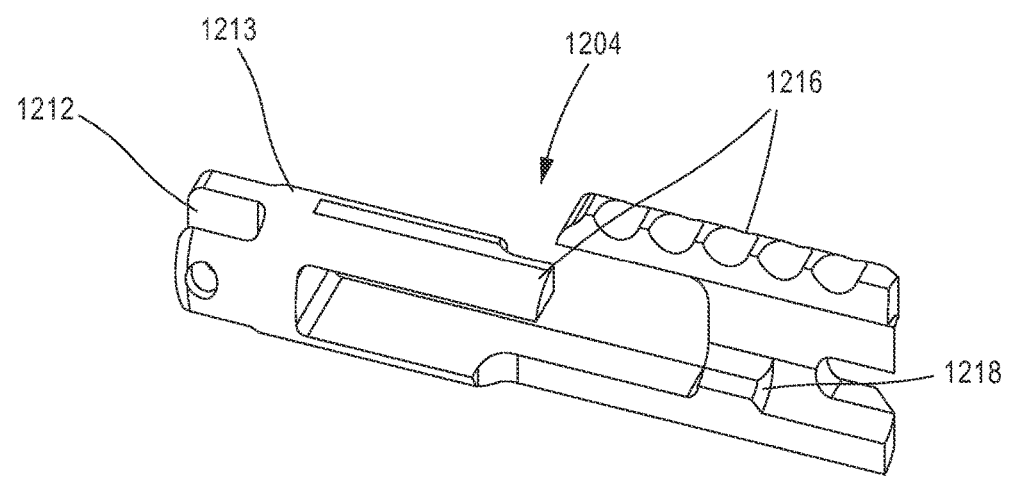
FIG. 32 is a perspective view of a rod tip connector assembly with a portion cutaway to illustrate internal aspects thereof, in accordance with aspects of the present disclosure.

As shown in the enlarged view of FIGS. 31 and 32, the rod tip connector assembly 1204 may include a hinge channel 1212 at a distal end 1213 for rotatably coupling one end of the link 1206 to the rod tip connector assembly 1204. Upper and lower flexing beams 1216 may be configured to flex in opposite directions to allow the tip end 1116 of the actuation shaft 1114 to clip in behind the detents 1218 provided on each of the flexing beams 1216.

Figure 33:
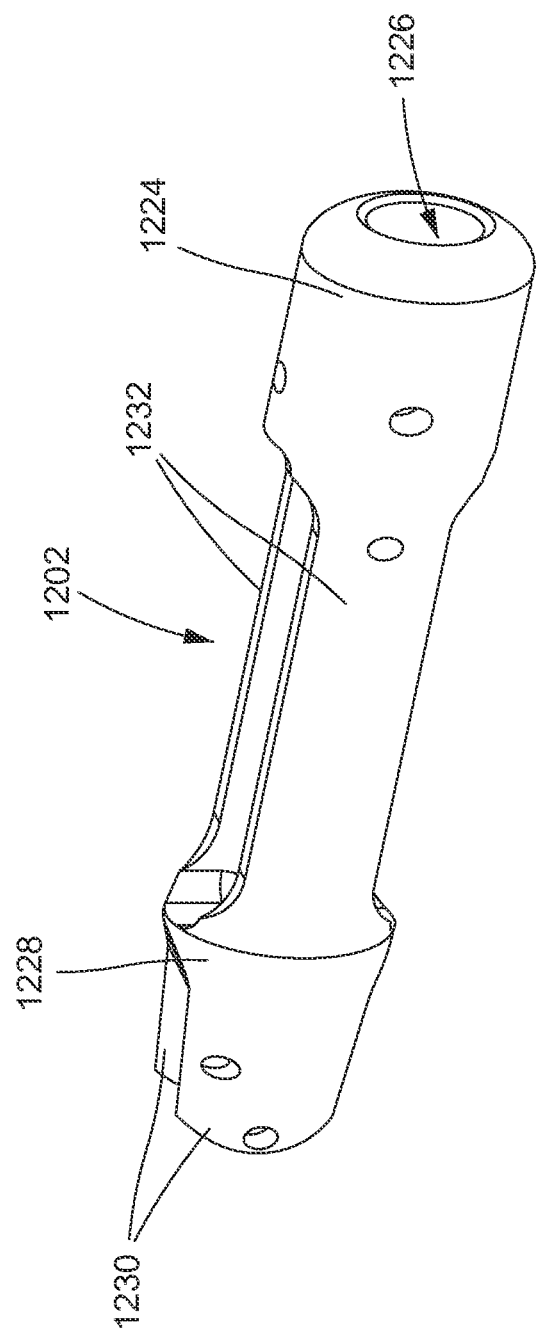
FIG. 33 is a perspective view of a clevis, in accordance with aspects of the present disclosure.

As shown in the enlarged view of FIG. 33, the clevis 1202 may include a proximal end portion 1224 with a clevis receiving hole 1226 for receiving the shaft assembly 1100 when coupling the end effector assembly 1200 onto the shaft assembly 1100. A distal end portion 1228 of the clevis 1202 may be formed with mounting arms 1230 that have various through-holes provided for hinge pins to be mounted for support and actuation of the jaws at the distal end 1228 of the clevis 1202. The distal end portion 1228 and the proximal end portion 1224 of the clevis 1202 may be joined by one or more main longitudinal support beams 1232.

Figure 34:
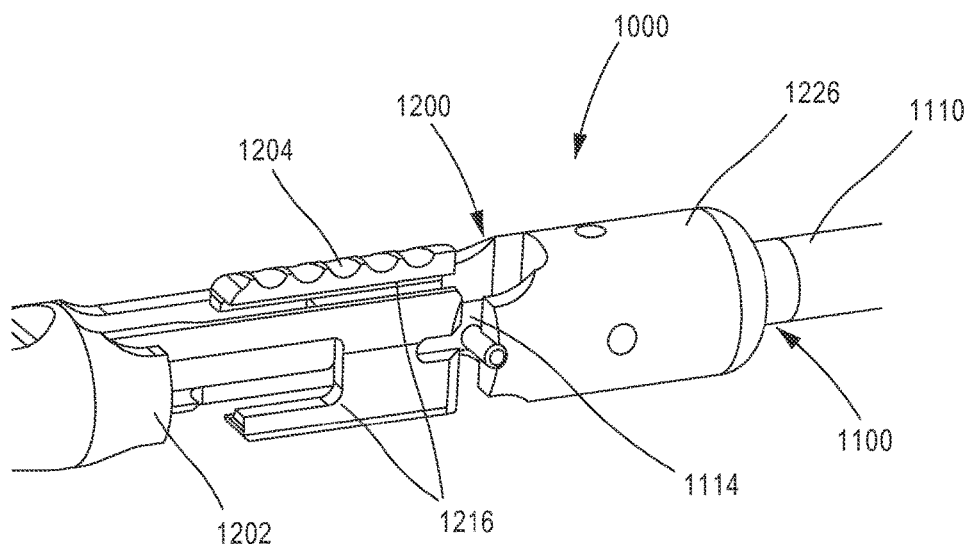
FIG. 34 is a perspective view of the end effector actuation system of FIG. 29 in a state of use, in accordance with aspects of the present disclosure.
Figure 35:
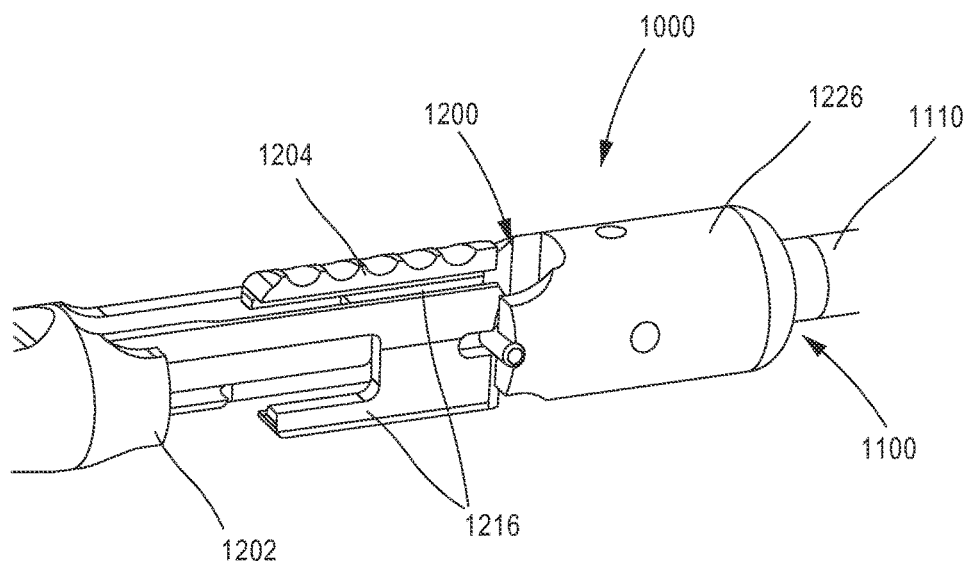
FIG. 35 is a perspective view of the end effector actuation system of FIG. 29 in another state of use, in accordance with aspects of the present disclosure.

As shown in FIG. 34, when the tip connector assembly 1204 is in the forward position the two flexing beams 1216 may flex to allow the actuation shaft 1114 to clip in place. As shown in FIG. 35, when the tip connector assembly 1204 is pulled proximally, a flex prevention slot 1240 on the proximal portions of each of the two flexing beams 1216 moves into a flex prevention pin 1242 on the clevis 1202. With the flex prevention slots 1240 engaged with the flex prevention pins 1242, the flexing beams 1216 are prevented from flexing up or down and thus the actuation shaft 1114 is prevented from dislodging from the rod tip connector assembly 1204. Continued proximal movement of the actuation shaft 1114 forces closure of the upper and lower jaws 1208 and 1210.

To release the end effector assembly 1200, the actuation shaft 1114 may be pushed into the forward position until the flex prevention slots 1240 disengage from the flex prevention pins 1242. Pressure may then be applied to each of the flexing beams 1216 in order to respectively push up and down the opposing flexing beams to release the tip end 1116 of the actuation shaft so the actuation shaft 1114 may move proximally past detents 1218, decoupling the actuation shaft 1114 from the tip connector 1204. The outer shaft 1110 may then be disengaged from the clevis 1202 and the end effector assembly 1200 disengaged from the shaft assembly 1100.

It is to be understood that any feature described in relation to any one aspect may be used alone, or in combination with other features described, and may also be used in combination with one or more features of any other of the disclosed aspects, or any combination of any other of the disclosed aspects.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. An end effector actuation system comprising:
   a shaft assembly including an outer shaft having an internal lumen and an actuation rod slidably received in the lumen, the outer shaft having a distal end portion that is compressible only when the actuation rod is absent from the lumen in the distal end portion;
   a locking boss provided on the distal end portion; and
   an end effector assembly having a receiving opening and at least one retention pocket,
   wherein the receiving opening is sized to receive the compressed distal end portion of the outer shaft and the at least one retention pocket is sized to receive the locking boss when the distal end portion is uncompressed due to the presence of the actuation rod in the lumen of the distal end portion, and
   wherein the at least one retention pocket is dimensioned to correspond with a dimension of the locking boss such that the locking boss is seated in a locked relationship when the distal end portion is uncompressed to prevent axial movement of the outer shaft in a distal direction relative to the end effector and such that rotation of the shaft assembly will result in rotation of the end effector assembly.

2. The end effector actuation system of claim 1, wherein at least one flexing slit is formed in the distal end portion of the outer shaft.

3. The end effector actuation system of claim 1, wherein a first flexing slit and a second flexing slit are formed in the distal end portion of the outer shaft, the first flexing slit being formed in the outer shaft at a position diametrically opposed to the second flexing slit to form a first flexing arm and a second flexing arm.

4. The end effector actuation system of claim 3, wherein the locking boss is provided on one of the first flexing arm or the second flexing arm.

5. The end effector actuation system of claim 4, further comprising:
   a handle assembly coupled to the shaft assembly.

6. The end effector actuation system of claim 5, wherein a proximal end portion of the outer shaft is secured to the handle assembly such that the actuator rod extends from the proximal end portion of the outer shaft and is slidably received into a main body portion of the handle assembly.

7. The end effector actuation system of claim 6, further comprising a locking sleeve configured on the outer shaft, the locking sleeve having a shaft lock receptacle for securely coupling the handle assembly to the outer shaft.

8. The end effector actuation system of claim 5, wherein the actuator rod has a lock ball formed on a proximal end thereof, and wherein the handle assembly includes a lever, the lever configured to engage the lock ball to control extension and retraction of the actuation rod through the lumen of the outer shaft.

9. The end effector actuation system of claim 1, wherein the end effector assembly further includes a spring retainer biased into a first position by a spring, the spring retainer providing a seat for application of force by the actuation rod to move the spring retainer into a second position.

10. The end effector actuation system of claim 9, wherein the end effector assembly comprises a multiple jaw configuration, and wherein movement of the spring retainer from a first position to a second position causes the multiple jaw configuration to open or close.

11. An end effector actuation system comprising:
   a shaft assembly having an outer shaft and an actuation shaft slidably received in the outer shaft, the actuation shaft having a tip end; and
   an end effector assembly including a clevis housing, a tip connector for securing the tip end of the actuation shaft, and a jaws assembly coupled to the tip connector,
   wherein the tip connector is housed in the clevis housing and has an expandable portion for receiving the tip end of the actuation shaft, the expandable portion being expandable only when the tip connector is at a predetermined position in the clevis housing,
   wherein the expandable portion comprises a plurality of collet petals that form a collet opening for receiving a ball end of the actuation shaft, wherein the clevis housing includes a plurality of support beams and at least one flexible grip beam radially spaced in between the support beams, wherein the plurality of support beams and at least one flexible grip beam form a clevis void region into which the collet petals can expand when the actuation shaft is in a first predetermined position, and wherein the at least one flexible grip beam extends cantilevered from a distal end portion of the clevis housing.

12. The end effector actuation system of claim 11, wherein the clevis housing further includes a clevis restriction area that restricts expansion of the collet petals when the actuation shaft is in a second predetermined position.

13. The end effector actuation system of claim 11, wherein the outer shaft includes a locking mechanism for releasably coupling the outer shaft to the end effector assembly.

14. The end effector actuation system of claim 11, wherein the jaws assembly includes an upper jaw and a lower jaw, and wherein each of the upper jaw and the lower jaw are attached to one end of a link, the other end of the link being rotatably attached to the tip connector.

15. The end effector actuation system of claim 11, wherein the plurality of support beams are secured to the distal end portion and a proximal end portion of the clevis housing.

16. A method of connecting an end effector to an actuation shaft, the method comprising:

providing a shaft assembly comprising:
 an outer shaft having a compressible distal end portion configured with at least one locking boss;
 an actuation shaft slidably accommodated in the outer shaft, one end of the actuation shaft configured to slidably extend and retract from the distal end portion of the outer shaft;

providing an end effector assembly having a receiving opening and at least one retention pocket for mating with the locking boss, the at least one retention pocket being dimensioned to correspond with a dimension of the locking boss such that the locking boss is seated in a locked relationship with the retention pocket when the distal end portion is uncompressed to prevent axial movement of the outer shaft in a distal direction relative to the end effector;

with the actuation shaft substantially retracted from the distal end portion of the shaft assembly, inserting the distal end portion of the shaft assembly into the receiving opening of the end effector to force compression of the distal end portion until the locking boss is received in the at least one retention pocket and the distal end portion uncompresses;

actuating the actuation shaft to extend into the distal end portion to prevent compression of the distal end portion and seat the locking boss in the at least one retention pocket in a locked relationship such that rotation of the shaft assembly will result in rotation of the end effector assembly.

17. The method of claim 16, further comprising:
providing a first flexing slit and a second flexing slit in the distal end portion of the outer shaft, wherein at least one flexing arm is formed between the first flexing slit and the second flexing slit.

18. The method of claim 17, wherein the locking boss is provided on the at least one flexing arm.

19. The method of claim 16, further comprising:
coupling a handle assembly to the shaft assembly to control the end effector via the actuation shaft.

* * * * *